(12) United States Patent
Anand et al.

(10) Patent No.: US 11,904,318 B2
(45) Date of Patent: Feb. 20, 2024

(54) CONCENTRATION ENRICHMENT, SEPARATION AND CATION EXCHANGE IN WATER-IN-OIL DROPLETS

(71) Applicant: Iowa State University Research Foundation, Inc., Ames, IA (US)

(72) Inventors: Robbyn K. Anand, Ames, IA (US); Sungu Kim, Ames, IA (US); Baskar Ganapathysubramanian, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 196 days.

(21) Appl. No.: 17/450,931

(22) Filed: Oct. 14, 2021

(65) Prior Publication Data

US 2022/0111386 A1   Apr. 14, 2022

Related U.S. Application Data

(60) Provisional application No. 63/198,373, filed on Oct. 14, 2020.

(51) Int. Cl.
| | | |
|---|---|---|
| *G01N 33/68* | (2006.01) | |
| *G01N 21/33* | (2006.01) | |
| *G01N 21/64* | (2006.01) | |
| *G01N 33/52* | (2006.01) | |
| *C07C 309/65* | (2006.01) | |

(Continued)

(52) U.S. Cl.
CPC ..... *B01L 3/502792* (2013.01); *B01L 3/50273* (2013.01); *B01L 3/502707* (2013.01); *B01L 3/502715* (2013.01); *B01L 2200/0673* (2013.01); *B01L 2200/0689* (2013.01); *B01L 2200/12* (2013.01); *B01L 2200/16* (2013.01); *B01L 2300/0645* (2013.01);

(Continued)

(58) Field of Classification Search
CPC ......... B01L 3/502792; B01L 3/502707; B01L 3/502715; B01L 3/50273; B01L 2200/0673; B01L 2200/0689; B01L 2200/12; B01L 2200/16; B01L 2300/0645; B01L 2300/0681; B01L 2300/0896; B01L 2300/12; B01L 2400/0421; B01L 3/502761; B01L 3/502784; B01L 3/502753; C12M 23/16; C12M 47/06

See application file for complete search history.

(56) References Cited

U.S. PATENT DOCUMENTS

2018/0094294 A1* 4/2018 Quake ................ G01N 15/1484

OTHER PUBLICATIONS

Saucedo-Espinosa et al. ("In-droplet electrophoretic separation and enrichment of biomolecules." Analytical chemistry 92.12 (Year 2020): 8414-8421) (Year: 2020).*

(Continued)

*Primary Examiner* — Jennifer Wecker
*Assistant Examiner* — Oyeleye Alexander Alabi
(74) *Attorney, Agent, or Firm* — McKee, Voorhees & Sease, PLC

(57) ABSTRACT

Microfluidic devices and methods that utilize ion concentration polarization within water-in-oil nanoliter scale droplets for concentration enrichment, separation, and substitution of charges species are disclosed. Such devices and methods can be used for separation of multiple species by mobility of each species and for the alteration and manipulation of the droplet composition by ion exchange.

20 Claims, 28 Drawing Sheets
(28 of 28 Drawing Sheet(s) Filed in Color)

(51) Int. Cl.
    C07C 309/73     (2006.01)
    A01N 1/02       (2006.01)
    G01N 1/40       (2006.01)
    B01L 3/00       (2006.01)
(52) U.S. Cl.
    CPC ............... B01L 2300/0681 (2013.01); B01L
            2300/0896 (2013.01); B01L 2300/12
            (2013.01); B01L 2400/0421 (2013.01)

(56) References Cited

OTHER PUBLICATIONS

Oh, Yoonjee, et al. ("Capillarity ion concentration polarization for spontaneous biomolecular preconcentration mechanism." Biomicrofluidics 10.1 (2016): 014102.) (Year: 2016).*

Chen et al., "Enhancing Protease Activity Assay in Droplet-Based Microfluidics Using a Biomolecule Concentrator" Journal of the American Chemical Society, vol. 133, pp. 10368-10371, 2011.

Saucedo-Espinosa et al., "In-Droplet Electrophoretic Separation and Enrichment of Biomolecules", Analytical Chemistry, vol. 92, pp. 8414-8421, 2020.

He et al., "Concentrating Solutes and Nanoparticles within Individual Aqueous Microdroplets", Analytical Chemistry, vol. 76, No. 5, pp. 1222-1227, 2004.

Kim et al., "Concentration Enrichment, Separation, and Cation Exchange in Nanoliter-Scale Water-in-Oil Droplets", Journal of the American Chemical Society, vol. 142, No. 6, pp. 3196-3204, 2020.

Park et al., "In-droplet microparticle separation using travelling surface acoustic wave", Biomicrofluidics, vol. 11, https://doi.org/10.1063/1.5010219, pp. 064112-064112-10, 2017.

Petersson et al., "Sample enrichment in a single levitated droplet for capillary electrophoresis", Journal of Chromatography, vol. B, No. 714, pp. 39-46, 1998.

Sanghavi et al., "Electrokinetic Preconcentration and Detection of Neuropeptides at Patterned Graphene-Modified Electrodes in a Nanochannel", Analytical Chemistry, vol. 86, pp. 4120-4125, 2014.

Yu et al., "An on-demand nanofluidic concentrator", Lab Chip, vol. 15, pp. 1524-1532, 2015.

* cited by examiner

Remove PDMS &
Bake on a hot plate for 10 min

Overlay channel PDMS &
Bake at 65 °C for 10 min

CONCENTRATION ENRICHMENT, SEPARATION AND CATION EXCHANGE IN WATER-IN-OIL DROPLETS

CROSS-REFERENCE TO RELATED APPLICATIONS

This application claims priority under 35 U.S.C. § 119 to provisional application Ser. No. 63/198,373, filed Oct. 14, 2020, herein incorporated by reference in its entirety.

GOVERNMENT RIGHTS

This invention was made with government support under National Science Foundation Grant Nos. CHE1849109 and DMR1435587. The government has certain rights in this invention.

FIELD OF THE INVENTION

The present invention is related to in-droplet concentration enrichment and separation of charged species. Specifically, as water-in-oil droplets are in simultaneous contact with the opposite poles of two polarized permselective membranes, ion concentration polarization causes an ion depleted zone and ion enriched zone within the droplet, enriching and separating charged species. Cation permselective membranes in such devices enable cation exchange within the droplet. Devices and methods such as are described herein allow for on-demand control over droplet composition. Such a microfluidic device and methods are disclosed herein.

BACKGROUND OF THE INVENTION

In droplet microfluidics, pico- to nanoliter-scale volumes are rapidly processed using functions that include merging, splitting and sorting, in-droplet mixing, and encapsulation of single particles. These features have been leveraged for droplet-templated synthesis of nano- and microparticles and for highly sensitive analyses, such as single-cell enzymatic assays or digital polymerase chain reaction, which benefit from partitioning a bulk sample into thousands to millions of reaction volumes. Droplet microfluidics allows for more exact quantification of specific biomolecules due to the ability to "digitize" a sample into discrete volumes or to encapsulate a single bead or cell per drop. However, following encapsulation, there are limited means by which droplet composition can be altered. This limitation is important for three reasons. First, the concentration of each reagent is critical to the reaction rate and, in assays, to signal intensity. Therefore, there is a need for methods that enrich the concentration of reagents and/or analytes within a droplet. Second, in the synthesis of particles, a gradient in composition may be desired for applications in which two poles of the resulting particle catalyze distinct reactions, and therefore, an ability to spatially separate droplet contents would be beneficial. Similarly, adoption of mobility-shift assays or reactions that result in a mixture of products requires a means of in-droplet separation. Third, benchtop assays and synthetic strategies benefit from the ability to add and extract reagents and products in a controlled manner. It is a goal of the present invention to utilize ion concentration polarization in-droplet for concentration enrichment, separation, and substitution of charges species.

Ion concentration polarization ("ICP") is an electrokinetic phenomenon in which ionic species are locally enriched and depleted at opposing ends of an ion permselective structure or a bipolar electrode under a voltage bias. When propagated with two ion selective membranes in series, neighboring ion enriched and depleted zones result. During ICP, the low ionic conductivity of the ion depleted zone ("IDZ") leads to a strong (>10-fold) local enhancement of the electric field and the formation of concentration and electric field gradients at the IDZ boundary. The nonlinear migration of ions in these gradients results in further exclusion of charged species from entering the IDZ, a feature that has been leveraged for focusing and continuous separation of charged species. ICP has had a major impact in several areas of application including desalination, enrichment and separation of trace analytes and bioparticles, cellular dielectrophoresis, regeneration of sensing substrates, mobility shift assays for bioanalysis, micelle-based extraction of uncharged compounds, and removal of excess fluid from blood.

There are existing methods that accomplish concentration enrichment in the context of water-in-oil ("W/O") droplets. Yu et al. describe a method in which ICP enriched dye-linked bovine serum albumin is sent to a droplet generator with the strategy to "lock in" the $10^4$-fold enrichment. *An On-Demand Nanofluidic Concentrator*, 6 Lab Chip 1524 (2015). Chen et al. reports a 10-fold reduction in assay time by sending ICP-enriched cell lysate to a droplet generator following the 16-fold enrichment of matrix metalloproteinases from diluted cellular supernatant. *Enhancing Protease Activity Assay in Droplet-Based Microfluidics Using a Biomolecule Concentrator* 133 J. Am Chem. Soc. 10368 (2011). However, both methods are limited to application prior to droplet generation. To achieve enrichment of solutes after a sample is encapsulated into droplets, Sanghavi et al. demonstrate the extraction of analytes from droplets by microdialysis and then subsequent enrichment by ICP in microchannels. *Electrokinetic Preconcentration and Detection of Neuropeptides at Patterned Graphene-Modified Electrodes in a Nanochannel*, 86 Anal. Chem. 4120 (2014). This approach allows for sampling and enrichment of only a limited portion of the total droplet volume. Enrichment of the entire droplet contents has been accomplished by Petersson et al. and He et al. via evaporation or with traveling surface acoustic waves for droplet-confined beads by Park et al. *Sample Enrichment in a Single Levitated Droplet for Capillary Electrophoresis*, 714 J. Chromatogr., Biomed Appl. 39 (1998); *Concentrating Solutes and Nanoparticles within Individual Aqueous Microdroplets* 76 Anal, Chem. 1222 (2004); *In-Droplet Microparticle Separation Using Travelling Surface Acoustic Wave*, 11 Biomicrofluidics 064112 (2017). However, these approaches are limited in throughput and scope, respectively. Further, there remains a need for rapid and universal methods to manipulate droplet composition.

Accordingly, it is an objective of the disclosure to provide devices and methods utilizing ICP in nanoliter-scale W/O droplets for concentration enrichment and separation of charged compounds from the entire volume of a droplet. It is a further objective of the disclosure to provide devices and methods utilizing ICP for separation of multiple species by mobility of each species. It is a further objective of the disclosure to provide devices and methods for ICP in nanoliter-scale W/O droplets for the alteration and manipulation of the droplet composition by cation exchange. It is a further objective of the disclosure to provide devices and methods utilizing ICP to control solute concentration within droplets thereby influencing the speed and sensitivity of assays. It is a further objective of the disclosure to provide devices and methods utilizing ICP to control solute concentration within droplets thereby influencing reaction rate and sensitivity.

Other objects, advantages and features of the present invention will become apparent from the following specification taken in conjunction with the accompanying examples or drawings.

BRIEF SUMMARY OF THE INVENTION

In one aspect, the present disclosure provides a microfluidic device comprising at least one fluidic main microchannel, wherein the one or more fluidic main microchannel is connected to at least one inlet and at least one outlet, wherein water-in-oil droplets are infused through the at least one of the inlet(s), flow through the at least one main microchannel, and are withdrawn from at least one of the outlet(s), and at least two permselective membranes, wherein a portion of each membrane extends into the main microchannel along a portion of the length of the main microchannel and a portion of each membrane extends outside of the main microchannel for electrical connection, and wherein the droplets are in simultaneous contact with a portion of the permselective membranes as the droplets flow through the main microchannel, and wherein a voltage bias is applied across the permselective membranes for in-droplet enrichment and separation of charged species within the droplet. In another aspect, the at least one main microchannel comprises two permselective membranes.

In another aspect, the permselective membranes extend into the main microchannel on opposite sides of the main microchannel. In another aspect, the permselective membranes extend into the main microchannel for about the entire length of the main microchannel, for at least about half the length of the main microchannel, and/or for at least about three-quarters the length of the main microchannel.

In an aspect, the microfluidic device further comprises at least two auxiliary channels wherein the portion of the permselective membrane that extends outside of the main microchannel extends into a portion of an auxiliary channel wherein the auxiliary channel comprises an electrolyte solution, and wherein the permselective membranes do not extend into the same auxiliary channel. In another aspect, the auxiliary channel further comprises driving electrodes to apply the voltage bias across the permselective membranes. In a further aspect, the permselective membranes are cation-selective and/or anion-selective.

In an aspect, the microfluidic device comprises more than one main microchannel in fluid connection with a singular inlet or more than one inlets. In another aspect, the microfluidic device comprises more than one main microchannel in fluid connection with a singular outlet or more than one outlet.

In an aspect, the microfluidic device comprises more than one main microchannel, wherein any two permselective membranes extends into only one main microchannel, or a portion of more than one main microchannel. In another aspect, the device comprises more than one main microchannel wherein the permselective membranes each extend into a unique auxiliary channel. In yet another aspect, the device comprises more than one main microchannel wherein at least two permselective membranes extend into the same auxiliary channel.

In an aspect, the permselective membranes have a size and dimension such that the membranes run parallel on either side of the at least one main microchannel and extend into the main microchannel along the length of the main microchannel for a length necessary for ion concentration polarization to occur across the entire droplet volume as the droplet flows through the main microchannel. In another aspect, ion concentration polarization occurs over the entire droplet volume.

In another aspect, the microfluidic device further comprises uniform flow of the droplets from the at least one inlet to the at least one outlet. In an aspect, uniform flow is ensured by a pump at an inlet to infuse the droplets into the device and/or a pump at an outlet to withdraw the droplets from the device and/or a syringe at an inlet to infuse the droplets into the device and/or a syringe at an outlet to withdraw the droplets from the device. In an aspect, the droplet flow rate is from about 0.0 μm/s to about 5000 μm/s. In another aspect, droplets flow from inlet to outlet in at least about 20 seconds, at least about 15 seconds, at least about 10 seconds, at least about 5 seconds or at least about 1 second.

In an aspect, the at least one main microchannel of the microfluidic device has a length of about 5.0 mm to about 100 mm, a width of about 10 μm to about 1000 and/or a height of about 10 μm to about 1000 In another aspect, the walls, ceiling, and/or floor of the main microchannel comprise polydimethylsiloxane ("PDMS"), polymethylmethacrylate ("PMMA"), polystyrene, polycarbonate, cyclic olefin polymer, cyclic olefin copolymer, pressure sensitive adhesive tape, silicon, glass, resin of a 3D printer, polyethylene glycol, crosslinked polyethylene glycol diacrylate ("PEGDA") resin, or combinations thereof.

In an aspect, volume of the droplets is from about 10 pL to about 50.0 nL. In another aspect, droplets comprise proteins, antigens, bioparticles, bacteria, virus, nucleic acids, enzymes, biological cells, DNA, RNA, aptamers, antibodies, peptides, peptide nucleic acids, morpholino oligonucleotides, receptors, other bioparticles, other nano particles, or a combination thereof. In yet another aspect the droplets comprise blood, blood plasma, saliva, urine, sweat, tears, or any other such biofluid or any combination thereof. In yet another aspect, the droplets comprise an electrolyte solution, phosphate buffer, Tris buffer, and/or combinations thereof.

In an aspect, the length of the permselective membranes is from about 1.0 mm to about 100 mm, the width of the permselective membranes is from about 50 μm to about 1000 μm, and/or the thickness of the permselective membranes is from about 1.0 μm to about 50 μm.

In an aspect, the auxiliary microchannels have a length of about 2.0 mm to about 100 mm, a width of about 10 μm to about 1000 μm, and/or a height of about 10 μm to about 1000 μm.

In an aspect, the walls, ceiling, and/or floor of the main microchannel comprise polydimethylsiloxane ("PDMS"), polymethylmethacrylate ("PMMA"), polystyrene, polycarbonate, cyclic olefin polymer, cyclic olefin copolymer, pressure sensitive adhesive tape, silicon, glass, resin of a 3D printer, polyethylene glycol, crosslinked polyethylene glycol diacrylate ("PEGDA") resin, or combinations thereof.

In an aspect, the electrolyte solution within the auxiliary channels comprises NaCl, KCl, $Na_2SO_4$, HCl, $H_2SO_4$, NaOH, KOH, $NaNO_3$, $KNO_3$, phosphate buffer, carbonate buffer, acetate buffer, borate buffer, Tris buffer, HEPES (4-(2-hydroxyethyl)-1-piperazineethanesulfonic acid), MOPS (3-(N-morpholino) propanesulfonic acid), TAE (Tris-acetate-EDTA), PIPES (piperazine-N,N'-bis(2-ethanesulfonic acid), tricine buffer, PBS (phosphate buffered saline) and/or combinations thereof.

In an aspect, the outlet of the main microchannel is connected to a droplet splitting device, and/or the outlet collects the droplets for further analytics and/or for further processing.

In an aspect, the voltage applied to the permselective membranes is between about 0 and about 500 V and/or the voltage applied to the electrolyte solution in the auxiliary channel is between about 0 V and about 500 V.

Disclosed herein is a method for concentration enrichment of charged species within a droplet comprising flowing water-in-oil droplets through at least one main microchannel of the microfluidic device of the invention and applying a voltage bias across the permselective membranes for a period of time so that ion concentration polarization occurs and therefore enrichment of charged species within a portion of the droplet. In an aspect, charged species are enriched 2- to 20-fold.

In an aspect of the method, the permselective membranes are cation-selective leading to concentration enrichment of anions in the droplet and/or the permselective membranes are anion-selective leading to a concentration enrichment of cations in the droplet.

In an aspect, the disclosed method comprises separation of charged species of varying and/or distinct electrophoretic mobilities occurs within a single droplet.

Disclosed herein is a method for ion exchange between the droplet and the electrolyte solution in an auxiliary channel comprising flowing water-in-oil droplets through at least one main microchannel of the microfluidic device of the invention and applying a voltage bias across the permselective membranes for a period of time so that ions are injected into the droplet from an auxiliary channel at the enriched portion of the droplet and ions are simultaneously ejected from the microdroplet into another auxiliary channel at the ion depleted portion of the droplet.

In an aspect of the method the permselective membranes are cation-selective and cation exchange occurs between the droplet and the electrolyte solution in an auxiliary microchannel and/or the permselective membranes are anion-selective and anion exchange occurs between the droplet and the electrolyte solution in an auxiliary microchannel. In an aspect, the electrolyte within the electrolyte solution is selected for specific ion exchange.

Disclosed herein is a method for cell lysis within a droplet comprising flowing water-in-oil droplets comprising at least one cell through at least one main microchannel of the microfluidic device of the invention and applying a voltage bias across the permselective membranes for a period of time so that cell lysis occurs within the droplet and the lysate is enriched and/or separated within the droplet.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1A:
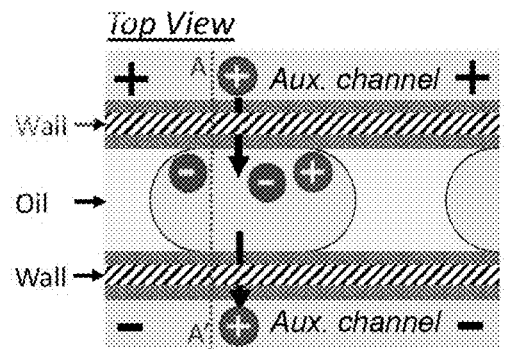
FIG. 1A is an illustration of a top-down view of a portion of a main microchannel comprising W/O droplets wherein walls of the main microchannel separate the main microchannel from two parallel auxiliary channels and permselective membranes parallel to the main microchannel and auxiliary channels each span a portion of the main microchannel and an auxiliary channel. A voltage bias is applied across the permselective membranes noted by a "+" in one auxiliary channel and a "−" in the other.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The present disclosure relates to microfluidic devices for concentration enrichment, separation and/or cation exchange in W/O droplets. The present disclosure includes microfluidic devices wherein W/O droplets flow through one or more main microchannels each of which comprises at least two permselective membranes, and/or at least two electrodes, such that charged species within the droplet undergo concentration enrichment. In an embodiment, charged species of varying mobility are separated within the droplet. In another embodiment, cation exchange occurs altering the composition of the droplet. The present disclosure further relates to methods of using the devices to electrokinetically enrich, and/or separate charged species within the droplet and/or manipulate and/or alter the droplet composition. The present disclosure provides a microfluidic device for concentration enrichment, separation and/or cation exchange in W/O droplets.

The embodiments described herein are not limited to any particular device or method of using the device, which can vary and are understood by skilled artisans based on the present disclosure herein. It is further to be understood that all terminology used herein is for the purpose of describing particular embodiments only, and is not intended to be limiting in any manner or scope. For example, as used in this specification and the appended claims, the singular forms "a," "an," and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation. The preferred materials and methods are described herein. In describing and claiming the embodiments of the present invention, the following terminology will be used in accordance with the definitions set out below.

The term "about," as used herein, refers to variations in size, distance or any other types of measurements that can be resulted from inherent heterogeneous nature of the measured objects and imprecise nature of the measurements itself. The term "about" also encompasses variation in the numerical quantity that can occur, for example, through typical measuring or handling procedures in the real world; through inadvertent error in these procedures; through differences in the manufacture, source, or purity of the ingredients used to make the device or carry out the methods, and the like. Whether or not modified by the term "about", the claims include equivalents to the quantities.

Microfluidic Devices

In one aspect, the present disclosure provides a microfluidic device for concentration enrichment, separation, and/or cation exchange in W/O droplets. The device comprises at least one inlet and at least one outlet, both in fluid connection with at least one main microchannel. The one or more fluidic main microchannels retain and move a solution comprising W/O droplets from inlet to outlet. Each main microchannel further comprises at least two permselective membranes. A portion of each permselective membrane extends into the main microchannel and along at least a portion of the length of the main microchannel for contact with the droplets retained within and/or moving through the main microchannel. Another portion of each permselective membrane extends outside of the main microchannel for electrical connection. In an aspect, at least two permselective membranes are not in physical contact with each other. In an embodiment, there are two permselective membranes per main microchannel and they each extend into the main microchannel at opposite sides of the main microchannel.

In an embodiment, the permselective membrane portion that extends outside of the main microchannel extends into a portion of an auxiliary channel, the auxiliary channel comprising an electrolyte solution. In another embodiment, the permselective membrane portion that extends outside of the main microchannel is in electrical connection with an electrode. In an embodiment, an electrode is placed in direct contact with the membrane. In another embodiment, an electrode is immersed in the electrolyte solution in the auxiliary channel.

In an aspect, more than one main microchannel is connected in series or in parallel with at least one other main microchannel, in fluid connection with the same or distinct inlet(s) and/or outlet(s). In an embodiment, a number of main microchannels may be grouped together and connected fluidly with another group or groups of microchannels. Within each group of microchannels any two main microchannels can be parallel to each other, on top of each other, or in another arrangement. A group of main microchannels may be in fluid connection with a singular inlet or many inlets. A group of main microchannels may be in fluid connection with a singular outlet or many outlets. In an embodiment, each main microchannel has unique permselective membranes. In an aspect, each main microchannel may have a unique set of auxiliary channels or the same auxiliary channel as any other main microchannel. In another aspect, any one auxiliary channel may have a unique electrolyte solution, or the same electrolyte solution as any other auxiliary channel. Many main microchannels may have permselective membranes that extend into the same auxiliary channel.

In an aspect, the main microchannel and the droplet are of the size and dimension such that the droplet is in physical contact with the at least two permselective membranes. In an embodiment, as the W/O droplet(s) move from inlet to outlet, a voltage bias is applied across the permselective membranes that extend into the main microchannel. In an embodiment, the voltage is applied to the electrolyte solution in the auxiliary channels using driving electrodes. In another embodiment, the voltage is applied to an electrode or other electrical contact in connection with the permselective membrane. In an aspect, voltage between the permselective membranes is such that they become polarized and form neighboring IDZ and an ion enriched zone ("IEZ") within a single droplet as it is retained within the main microchannel and/or moves from inlet to outlet through the main microchannel. In an embodiment, the main microchannel comprises two permselective membranes on opposite sides of the main microchannel and a voltage bias is applied across the two membranes such that they become polarized and form neighboring IDZ and an IEZ within a single droplet as it is retained within the main microchannel and/or moves from inlet to outlet through the main microchannel. The droplet contacts the positive pole of one membrane and the negative pole of another membrane.

In an embodiment, the permselective membranes are cation-selective. In another embodiment, cation exchange occurs between the droplet and the electrolyte solution in the auxiliary channels when a voltage bias is applied across two cation permselective membranes.

Figure 1B:
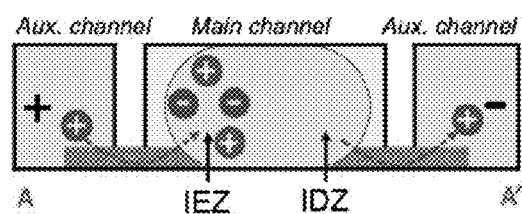
FIG. 1B is an illustration of a cross-sectional side view of the A-A' cut line in FIG. 1A.

An exemplary device is illustrated in FIG. 1A and FIG. 1B wherein the permselective membranes comprise cation selective membranes and run parallel to the main channel with a portion extending into the main microchannel and a portion extending into auxiliary channels which comprise an electrolyte solution. FIG. 1A illustrates a top-down view of a portion of a main microchannel comprising W/O droplets. The walls of the main microchannel separate the main microchannel from two parallel auxiliary channels. Two permselective membranes run parallel to the main microchannel and an auxiliary channel with a portion of the membrane extending into each the main microchannel and the auxiliary channel. A voltage bias is applied across the permselective membranes via driving electrodes in the auxiliary channels illustrated by a "+" in one auxiliary channel and a "−" in the other. In this disclosure, for convenience, in top-down oriented views, the membrane to which the voltage is applied is oriented in the top of the frame, image, or illustration and is therefore sometimes referred to as the "top" membrane and the droplet in contact with the "top" membrane is referred to as the "top" of the droplet. Likewise, the membrane connected to either ground or a negative voltage is oriented at the bottom of the frame, image, or illustration and is therefore sometimes referred to as the "bottom" membrane and the droplet in contact with the "bottom" membrane is referred to as the "bottom" of the droplet.

Under the applied voltage, cations are injected into the droplet at the top and extracted from the droplet at the bottom through the respective cation permselective membrane. Anions migrate toward the top to maintain electroneutrality and are therefore enriched generating an IEZ at the top of the droplet and an IDZ at the bottom of the droplet. FIG. 1B illustrates this redistribution of ionic species with a cross-sectional side view. FIG. 1B illustrates the cross-section of the cut line A to A' in FIG. 1A and therefore the top of the FIG. 1A is to the left side of FIG. 1B. FIG. 1B shows the IEZ and IDZ formation within the droplet that occurs as the droplet moves through the microchannel with a voltage bias applied across the permselective membranes. With the device and methods described herein, ICP occurs over the entire droplet volume.

Figure 2:
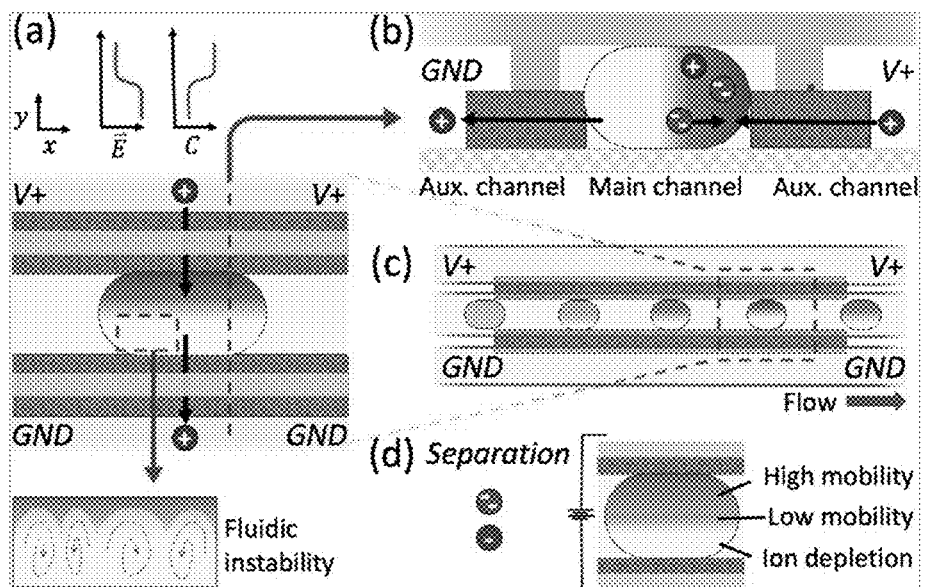
FIG. 2 is an illustration of enrichment and separation of charged species by concentration polarization inside droplets in a microfluidic channel.

FIG. 2 further depicts the device. Section (c) of FIG. 2 shows an illustration of the W/O droplets flowing through a portion of a main microchannel with a voltage bias applied between the permselective membranes. This is denoted by "V+" in the top auxiliary channel wherein a voltage is applied and "GND" in the bottom auxiliary channel which is connected to ground. As the droplet moves through the main microchannel it undergoes ICP, and IDZ and IEZ formation within the droplet occurs which is denoted by a shading of the droplet. A cross-section of one droplet is illustrated in section (b) of FIG. 2. Section (b) illustrates the cation injection into the droplet from the auxiliary channel through the permselective membrane wherein the voltage is applied and also illustrates the cation extraction from the droplet into the auxiliary channel wherein the permselective membrane is grounded. The IDZ is denoted by the light area and the IEZ by the shaded area. A top-down view of one droplet is depicted in section (a). This illustration shows the IDZ and IEZ zones via shading and also depicts the uneven boundary between the two zones in the inset due to fluidic instability within the droplet. Section (d) of FIG. 2 illustrates how separation of charged species occurs within a droplet as species with higher mobility migrate more towards the top of the droplet than species with lower mobility.

In an embodiment, the device further comprises a power source connected with the driving electrodes, wherein the power source is configured to supply a voltage in the range of from about 50 mV to about 500 V. In an aspect, the power source is a battery.

In an aspect, the device of the current disclosure comprises a device for uniform droplet flow through a main microchannel. Uniform flow may be ensured by any method commonly known in the art. In an embodiment, uniform pressure driven flow is ensured by a pump at an inlet to infuse into the device and/or a pump at an outlet to withdraw the solution from the device. In an embodiment, the droplets are infused into the inlet by a syringe and/or similarly withdrawn from the outlet using a syringe. In an aspect, droplet flow rate through a main microchannel is regulated by any known method in the art and further may be monitored and/or controlled with an inline flow rate sensor. In an embodiment, the droplet flow rate is from about 0.0 μm/s to about 5000 μm/s. In an embodiment, the device of the current disclosure comprises a droplet generator. In an aspect, the droplet generator is in fluid connection with the inlet of a main microchannel. In an aspect the droplet generator generates W/O droplets according to the method described herein and controls droplet flow through the main microchannel.

In an aspect, the outlet of the main microchannel may connect to one or more microchannel or groups of microchannels, and/or may connect to a droplet splitter such as a Y junction, and/or may be an outlet such that the droplets are collected for analytics or further processing.

In any of the microfluidic devices described herein part or all of the permselective membranes may be replaced by an electrode or other substance wherein faradaic processes at the electrode surface lead to ion exchange, and therefore ICP, within the droplets. In an embodiment, at least one main microchannel comprises electrodes in addition to, or in substitution of, the permselective membranes. In this embodiment, faradaic reactions inject and consume electrolyte ions.

In any of the microfluidic devices described herein part or all of the permselective membranes may be replaced by an electrode or other substance wherein oxidation and reduction reactions lead to ion exchange, and therefore in-droplet ICP occurs via electrochemical reactions as a means of ion transport. In an aspect, the electrode materials are selected such that the electrode undergoes oxidation or reduction, for example, at metal centers within the electrode, and inject and/or uptake ions for ion transport. In an aspect, the electrode comprises an ion insertion material such as is found in batteries.

In any of the microfluidic devices described herein part or all of the permselective membranes may be replaced by charged hydrogels wherein ion transport, and therefore ICP, occurs with or without an electric field applied.

Main Microchannel

As used herein, a microchannel is a passageway from at least one inlet to at least one outlet wherein fluid flows from inlet to outlet. As used herein, a main microchannel is the microchannel wherein W/O droplets flow from inlet to outlet and undergo ICP for concentration enrichment, separation, and/or cation exchange and/or cell lysis. As used herein, the length of a microchannel is the distance from inlet to outlet through the microchannel along the intended fluid flow. As used herein, the width of a microchannel is the horizontal distance of two points that are on the opposite edges of the cross-section perpendicular to the intended fluidic flow and are furthest away from each other. As used herein, the height of a microchannel is the vertical distance from the floor of a microchannel to the ceiling of the same.

As used herein, the main microchannel is referred to as having any width and height necessary to transport pico- to nano-liter scale W/O droplets. In an embodiment, the width of a main microchannel is from about to about 10 μm to about 1000 μm. In an embodiment, the height of a microchannel is from about 10 μm to about 1000 μm. The cross-section of a microchannel can have any two-dimensional shape, such as square, rectangular, circle, or a combination thereof. The length of a microchannel can be any length sufficient to allow in-droplet enrichment. In an embodiment, the length of a microchannel is from about 5.0 mm to about 100 mm. A microchannel may be straight or curved.

In an aspect, the walls, floor, and ceiling of the main microchannel of the device described herein can be composed of any material that will retain and move a solution comprised of W/O droplets from at least one inlet to at least one outlet. In an aspect, the main microchannel is not conductive other than any portion of the main microchannel that comprises a permselective membrane. In some embodiments, the walls, floor, and/or ceiling of the main microchannel comprise a polymeric material. In an embodiment, the walls, floor, and/or ceiling the main microchannel is comprised of polydimethylsiloxane ("PDMS"), polymethylmethacrylate ("PMMA"), polystyrene, polycarbonate, cyclic olefin polymer, cyclic olefin copolymer, pressure sensitive adhesive tape, silicon, glass or the like. In an embodiment, the walls, floor, and/or ceiling of the microchannels comprise the resin of a 3D printer. In an embodiment, the walls, floor, and/or ceiling of the microchannels comprise polyethylene glycol. In another embodiment, the walls of the microchannel comprise crosslinked polyethylene glycol diacrylate ("PEGDA") resin.

W/O Droplets

As used herein, a droplet is a pico- to nano-liter scale droplet comprising charged species in an aqueous solution. The aqueous solution is encapsulated in droplets suspended within an oil continuous phase. As used herein, water-in-oil means the encapsulated droplets as described herein suspended in a continuous oil phase. The droplets suspended in oil are in fluidic flow from at least one inlet through at least a portion of one main microchannel of the device described herein and to at least one outlet. In an embodiment, the volume of the droplets is from about 10 pL to about 50.0 nL. In an embodiment, the diameter of the droplets is from about 10 μm to about 1000 μm.

In an aspect, the droplets comprise any charged species for enrichment and/or separation, including but not limited to reaction reagents and/or an analyte. In an embodiment, droplets comprise charged species such as proteins, antigens, bioparticles, bacteria, virus, nucleic acids, enzymes, biological cells, DNA, RNA, aptamers, antibodies, peptides, peptide nucleic acids, morpholino oligonucleotides, receptors, other bioparticles, other nano particles, molecules, polyatomic ions, atomic ions or a combination thereof. In an embodiment, the aqueous solution within the droplet comprises blood, blood plasma, saliva, urine, sweat, tears, or any other such biofluid or any combination thereof.

In an aspect, the droplets comprise an electrolyte solution. As used herein an electrolyte solution is an electrically conducting solution comprising dissolved ions. In an embodiment, the electrolyte solution comprises a buffer. As used herein, a buffer is a solution that resists a shift in pH that would otherwise be cause by addition of an acid or base. This disclosure is meant to incorporate any electrolyte solution and/or buffer solution as commonly known to the skilled artisan. In an embodiment, the electrolyte solution comprises NaCl, KCl, $Na_2SO_4$, HCl, $H_2SO_4$, NaOH, KOH, $NaNO_3$, $KNO_3$ and/or combinations thereof. In an embodiment, the electrolyte solution comprises phosphate buffer, carbonate buffer, acetate buffer, borate buffer, Tris buffer, HEPES (4-(2-hydroxyethyl)-1-piperazineethanesulfonic acid), MOPS (3-(N-morpholino) propanesulfonic acid), TAE (Tris-acetate-EDTA), PIPES (piperazine-N,N'-bis(2-ethanesulfonic acid), tricine buffer, PBS (phosphate buffered saline) and/or combinations thereof. In an embodiment the droplets comprise an electrolyte solution utilized as a "background" electrolyte solution that comprises an analyte targeted for enrichment and/or separation. As used herein "background" refers to the contents of the droplet other than the charged particles intended for concentration enrichment and/or separation.

Permselective Membrane

As used herein, a permselective membrane is a semipermeable membrane that allows transport of certain dissolved ions, while blocking other ions or neutral species. The selectivity of the membrane is due to Donnan exclusion. The permselective membrane may be cation or anion selective. Preferred permselective membranes include Nafion™ membranes distributed by the Chemours Company. In a preferred embodiment, the permselective membranes are cation-selective.

The permselective membrane as described herein may have any size or dimension such that a portion extends into the main microchannel for contact with the droplets and another portion extends outside of the channel for electrical connection. As used herein, the length of a permselective membrane is the distance the membrane spans the length of the main microchannel along the intended fluid flow. In an embodiment, the permselective membrane extends into the main microchannel for the entire length of the main microchannel. In another embodiment, the permselective membrane extends into the main microchannel for at least about half the length of the main microchannel. In another embodiment, the permselective membrane extends into the main microchannel for at least about three-quarters of the length of the main microchannel. As used herein, the width of a permselective membrane is the horizontal distance of two points that are on the opposite edges of the cross-section of the membrane perpendicular to the intended fluidic flow and are furthest away from each other. As used herein, the thickness of a permselective membrane is the vertical distance from the bottom of a permselective membrane to the top of the same. In an embodiment, the width of a permselective membrane is from about to about 50 μm to about 1000 In an embodiment, the thickness of a permselective membrane is from about 1.0 μm to about 50 The cross-section of a permselective membrane can have any two-dimensional shape, such as square, rectangular, circle, or a combination thereof. The length of a permselective membrane can be any length sufficient to allow in-droplet concentration enrichment, separation, and/or cation exchange. In an embodiment, the length of a permselective membrane is from about 1.0 mm to about 100 mm. A permselective membrane may be straight or curved or have any top-down shape.

Auxiliary Microchannels and Electrolyte Solution

In an embodiment, the portion of a permselective membrane that extends outside of the main microchannel for electrical connection extends into an auxiliary microchannel which comprises an electrolyte solution. Auxiliary microchannels are separate from the main microchannel, and each main microchannel has at least two, one per permselective membrane. In an embodiment, driving electrodes are in electrical connection with the electrolyte solution within the auxiliary channel to drive the voltage bias across the permselective membranes.

In an aspect, auxiliary microchannels can be any size, shape, and/or dimension such that the auxiliary microchannel accommodates an electrolyte solution in connection with at least a portion of the permselective membrane and also accommodates driving electrodes for voltage bias application. In an embodiment, auxiliary channels run parallel to at least a portion of the main microchannel. In an embodiment, each main microchannel has a unique set of auxiliary microchannels. In another embedment, a portion of the permselective membrane extending outside of more than one microchannel also extends a portion of the permselective membrane into the same auxiliary channel. In an embodiment, the permselective membrane of several microchannels extend into one auxiliary microchannel. In some embodiments, a main microchannel and an auxiliary channel share a common wall, floor, and/or ceiling.

As used herein, an auxiliary microchannel is referred to as having any width, length, and height necessary to comprise an electrolyte solution. In some embodiments, the auxiliary microchannel has any width, length, and height necessary for a portion of the permselective membrane to extend into the auxiliary channel for electrical connection. In some embodiments, the auxiliary microchannel has any width, length, and height necessary for a driving electrode to apply a voltage to the permselective membrane. As used herein, the length, width and height of an auxiliary channel relates to the auxiliary channel's orientation as to the main microchannel. As used herein, the length of an auxiliary microchannel is the maximum distance of the auxiliary channel along the intended fluid flow of the main microchannel. As used herein, the width of an auxiliary microchannel is the horizontal distance of two points that are on the opposite edges of the cross-section of the auxiliary channel perpendicular to the intended fluidic flow of the main microchannel and are furthest away from each other. As used herein, the height of an auxiliary microchannel is the vertical distance from the floor of an auxiliary microchannel to the ceiling of the same. In an embodiment, the width of an auxiliary microchannel is from about to about 10 μm to about 1000 μm. In an embodiment, the height of a microchannel is from about 10 μm to about 1000 μm. The cross-section of a microchannel can have any two-dimensional shape, such as square, rectangular, circle, or a combination thereof. The length of an auxiliary microchannel can be any length sufficient to allow in-droplet concentration enrichment, separation, and/or cation exchange. In an embodiment, the length of a microchannel is from about 2.0 mm to about 100 mm.

In an aspect, the walls, floor, and/or ceiling of an auxiliary microchannel of the device described therein can composed of any material that will retain an electrolyte solution. In an aspect, the auxiliary microchannel is not conductive. In some embodiments, the walls, floor, and/or ceiling of the main microchannel comprises a polymeric material. In an embodiment, walls, floor, and/or ceiling the auxiliary microchannel is comprised of polydimethylsiloxane ("PDMS"), polymethylmethacrylate ("PMMA"), polystyrene, polycarbonate, cyclic olefin polymer, cyclic olefin copolymer, pressure sensitive adhesive tape, silicon, glass or the like. In an embodiment, the walls, floor, and/or ceiling of the auxiliary microchannels comprise the resin of a 3D printer. In an embodiment, the walls, floor, and/or ceiling of the auxiliary microchannels comprise polyethylene glycol. In another embodiment, the walls of the microchannel comprise cross-linked polyethylene glycol diacrylate ("PEGDA") resin.

In an aspect the auxiliary microchannel comprises an aqueous electrolyte solution. As used herein an electrolyte solution is an electrically conducting solution comprising dissolved ions. In an embodiment, the electrolyte solution comprises a buffer. As used herein, a buffer is a solution that resists a shift in pH that would otherwise be cause by addition of an acid or base. This disclosure is meant to incorporate any electrolyte solution and/or buffer solution as commonly known to the skilled artisan. In an embodiment, the electrolyte solution comprises phosphate buffer, Tris buffer, and/or combinations thereof.

In an aspect, a portion of the permselective membrane extends into the auxiliary channel for electrical connection. In an embodiment, the auxiliary channel comprises an electrolyte solution and further comprises one or more driving electrodes as a voltage source. In another embodiment, the auxiliary microchannel comprises a conductive epoxy connected to a voltage source. In another embodiment, the permselective membrane is in contact with an electrode for electrical contact to a voltage source. This disclosure is meant to incorporate any electrode and voltage source as commonly known to the skilled artisan.

Figure 3A:
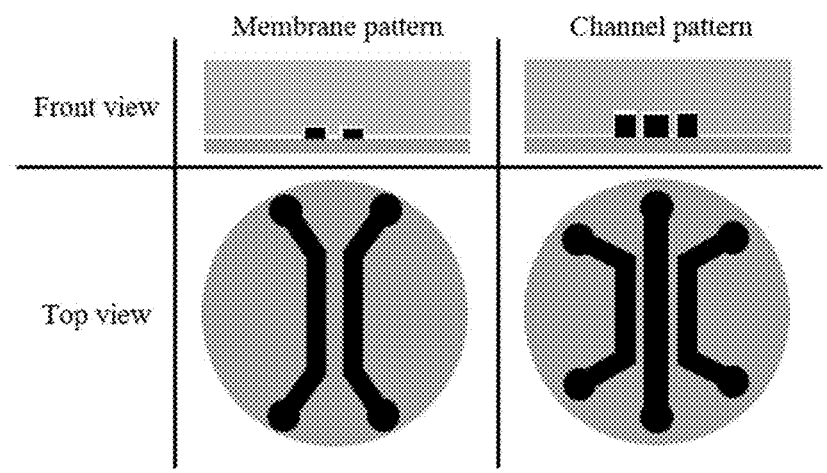
FIG. 3A depicts the first step in the device preparation procedure wherein both the microfluidic channels subsequently utilized for flow-patterning the membrane and the microfluidic channels comprising the main and auxiliary channels are each patterned by a caste-mold process into a PDMS monolith.
Figure 3B:
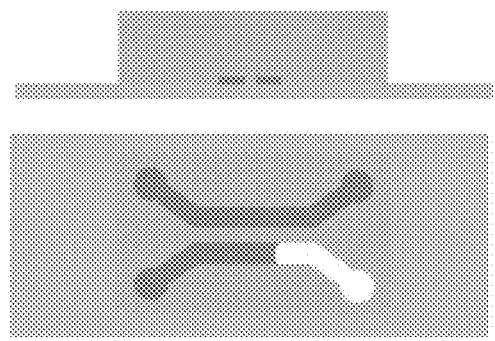
FIG. 3B depicts the second step in the device preparation procedure wherein the microfluidic channels defining the membrane pattern are placed on the glass slide and then the precursor for the permselective membranes is injected through punch holes that define the inlets to the microchannels.
Figure 3C:
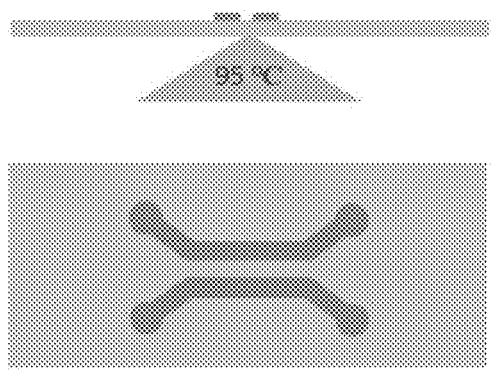
FIG. 3C depicts the third step in the device preparation procedure wherein the permselective membrane is cured on a hot plate and the PDMS monolith that defines the microchannels is removed.
Figure 3D:
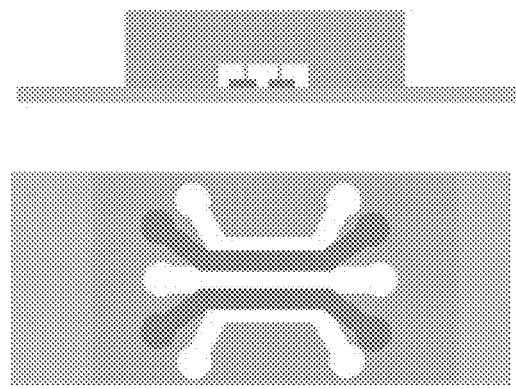
FIG. 3D depicts the fourth step in the device preparation procedure wherein the PDMS monolith imprinted with the main and auxiliary channels is aligned on top of the permselective membranes such that the each membrane contacts both the main channel and an auxiliary channel.

An exemplary device design comprising auxiliary microchannels comprising an electrolyte solution is shown in FIG. 3D. FIG. 3D illustrates a cross-section and a top-down view. The main microchannel is in the middle, flanked by two auxiliary channels. Two permselective membranes run along each side of the main microchannel and span a portion of the length of the main microchannel and a portion of an auxiliary microchannel.

Methods of Use

Methods described herein are meant to include any and all aspects and embodiments of the device and applications of using the same as described herein. The method that is herein described allows on-demand control over droplet composition including de-mixing, in which droplet contents are polarized into enriched and depleted zones, and selective exchange of ion content. This provides control over reaction rate in which the enriched and/or separated charged particles are reagents, detection limits in which the enriched and/or separated charged particles are analytes, and provides a means for dosing, gradual addition of reagents, or extraction of charged species without the need to alter droplet volume by splitting or merging. The devices and methods of using the devices described herein allow for more rapid, sensitive, and versatile droplet-based analysis and/or bioanalysis.

In an embodiment W/O droplets flow through at least one main microchannel and are withdrawn from the outlet. Uniform flow is ensured by any method commonly known in the art. In an embodiment, uniform pressure driven flow is ensured by a pump at an inlet to infuse into the device and/or a pump at an outlet to withdraw the solution from the device. In an embodiment, the droplets are infused into the inlet by a syringe and/or similarly withdrawn from the outlet using a syringe. In an embodiment the inlet and outlet are open reservoirs wherein uniform flow is gravity-driven, for instance by a fluid height differential, or a larger volume of fluid in the inlet than outlet, or by tilting the device such that the inlet is located in a higher plane than the outlet. In an embodiment, the inlet serves as a port for a larger receptacle to plug into the inlet. In another embodiment, the outlet comprises a receptacle to accept the droplets.

In another embodiment, the outlet is in fluid connection with a Y-junction or other device for droplet splitting which will separate the enriched and/or depleted portions. In an embodiment the outlet is connected to a device for droplet splitting and then to an inlet for another main microchannel as described herein for further in-droplet ICP. In another embodiment, the outlet is in fluid connection with another device for further droplet processing and/or analysis. In another embodiment the outlet is in fluid connection with an incubation area. In an embodiment, the incubation area comprises a microchannel wherein temperature is controlled. In an embodiment the incubation area comprises a temperature controlled microchannel wherein the microchannel is serpentine. In an embodiment, droplets from the outlet of the device and methods described herein improve the sensitivity of subsequent assays as droplets undergo enrichment just prior to readout. In another embodiment, the device and methods described herein are coupled with digital polymerase chain reaction to decrease the number of cycles required to reach the detection threshold.

In an aspect, droplet flow rate through a main microchannel is regulated by any known method in the art and further may be monitored and/or controlled with an inline flow rate sensor. In an embodiment, droplet flow rate is maintained and regulated by a pump. In another embodiment, droplet flow rate is maintained and regulated by a syringe pump. In an embodiment, the droplet flow rate is from about 0.0 µm/s to about 5000 µm/s. In an embodiment, droplets flow from inlet to outlet in at least about 20 seconds. In another embodiment, droplets flow from inlet to outlet in at least about 15 seconds. In another embodiment, droplets flow from inlet to outlet in at least about 10 seconds. In another embodiment, droplets flow from inlet to outlet in at least about 5 seconds. In another embodiment, droplets flow from inlet to outlet in at least about 1 second.

The devices and methods described herein provide a method for enriching charged particles within a droplet. In an aspect, as droplets flow through the main microchannel a voltage bias is applied across the at least two permselective membranes such that the two membranes become polarized creating IDZ and IEZ within the entire droplet flowing through the main microchannel in contact with the membranes. As used herein enrichment factor ("EF") is the increase in the concentration of the enriched species within the IEZ. In an aspect, the methods and devices described herein lead to 2- to 20-fold enrichment of an enriched species within a droplet. In an embodiment, the methods and devices described herein lead to at least about 2-fold enrichment. In an embodiment, the methods and devices described herein lead to at least about 3-fold enrichment. In an embodiment, the methods and devices described herein lead to at least about 4-fold enrichment. In an embodiment, the methods and devices described herein lead to at least about 5-fold enrichment. In an embodiment, the methods and devices described herein lead to at least about 6-fold enrichment. In an embodiment, the methods and devices described herein lead to at least about 7-fold enrichment. In an embodiment, the methods and devices described herein lead to at least about 8-fold enrichment. In an embodiment, the methods and devices described herein lead to at least about 9-fold enrichment. In an embodiment, the methods and devices described herein lead to at least about 10-fold enrichment. In an embodiment, the methods and devices described herein lead to at least about 20-fold enrichment.

In an embodiment, the permselective membranes are cation-selective membranes wherein anions within a droplet migrate against the IDZ which repels it electrostatically thereby leading to concentration enrichment of anions in the IEZ of the droplet.

In another aspect, the devices and methods described herein provide a method for enriching and/or separating charged particles within a droplet. In an embodiment, charged particles of varying and/or distinct electrophoretic mobilities are separated within a single droplet. Charged particles of varying and/or distinct electrophoretic mobilities migrate to varying areas within a droplet, wherein charged particles of higher mobility migrate further to the edge of the droplet away from the IDZ and charged particles with lower mobility focus more toward the middle of the droplet and closer to the IDZ than the higher mobility particles creating tiers of enrichment. The separation enables fractionation prior to droplet splitting.

In another aspect, the devices and methods described herein provide a method for cell lysis wherein a cell within a droplet ruptures and the lysate is enriched and/or separated within the droplet as the droplet moves through the main microchannel with permselective membranes under a voltage bias. Without being limited to a particular theory or method, there are three different mechanisms which may explain cell lysis in the droplet. The first is applying an electric current to the droplet increases electric field, the electric field is then further enhanced from redistributed electrolyte concentration with the highest electric field near the cathodic membrane, and the high local electric field lyses the cells by breaking the cell membrane. A second mechanism is wherein charge neutrality breaks down inside the depletion zone within the droplet resulting in non-zero charge density and fluid flow is driven by the electric field at this non-zero charge density area, wherein the shear stress from the fluid flow mechanically lyses the cell. The third mechanism is osmotic cell lysis wherein when the electrolyte concentration around the cell is low, the cell uptakes water from the surrounding solution resulting in swelling over time and eventually the cell ruptures due to high pressure inside the cell.

In another aspect, the devices and methods described herein provide a method for ion exchange between the droplet and an electrolyte solution in an auxiliary microchannel as the droplet moves through the main microchannel with permselective membranes under a voltage bias. In an aspect, the electrolyte solution in the auxiliary channel may be a source of cations and/or anions for cation and/or anion exchange within the droplet. In an embodiment, the permselective membranes are cation-selective and cation exchange occurs between the droplet and the electrolyte solution as the droplet moves through the main microchannel with permselective membranes under a voltage bias. The methods and devices described herein allow for modification of droplet composition "on the fly", without alteration of droplet volume. The magnitude of the ion selective current, as controlled by the applied voltage and the serial resistances of the membranes and droplet, control the rate at which ionic charge is injected.

Several parameters may influence the time scale and extent of in-droplet enrichment, such as droplet length along the channel axis, velocity of the droplet, electric field strength, bulk concentration of the electrolyte, and the electrophoretic mobilities of the charged species in the droplet. Generally, maximum enrichment is found in smaller droplets, under higher voltage, and with droplets having lower background ionic strength. As used herein "background" refers to the contents of the droplet other than the charged particles intended for concentration enrichment and/or separation.

EF is positively correlated to voltage bias. Without being limited to a particular mechanism or theory, higher voltages generally correlate to larger IDZ within the droplet focusing the charged particles in a smaller IEZ, therefore creating higher local EF. Furthermore, time for enrichment is shortened by higher field strength because of stronger repulsion of charges from the IDZ. However, very high field strength may cause vortex flow patterns that disrupt separation by causing mixing.

EF is negatively correlated to ionic strength within the droplet. Without being limited to a particular mechanism or theory, the charged compound within the droplet carries a significant fraction of the ionic current. This fraction is increased at lower background electrolyte concentration within the droplet, which leads to a higher EF. Without limiting to a particular method or theory, with devices comprising cation-selective membranes, the effect may be due to the relative ability of the anion to migrate towards the anionic end of the droplet where cations enter, to maintain electroneutrality and therefore there is greater enrichment with a low mobility background electrolyte anion.

In larger droplets, maximum EF peaks earlier than in smaller droplets, and may thereafter decay to a lower steady state value. Larger IDZ generally corresponds to higher EF. As the droplets get larger, the correlation may diminish as the efficiency of ICP is diminished.

In an aspect, IDZ size and shape within the droplet is distorted by the fluidic flow of the droplet through a main microchannel. In-droplet IDZ is distorted by the fluid flow and becomes asymmetrical. However, there is no gross mixing of the contents or the IDZ and IEZ. This lack of mixing between the upper and lower halves of the droplet can be attributed to known fluidic patterns that develop in flowing droplets as separate circulating flows develop in each half.

All publications, patent applications, issued patents, and other documents referred to in this specification are indicative of the level of ordinary skill in the art to which this invention pertains and are herein incorporated by reference to the same extent as if each individual publication or patent application was specifically and individually indicated as incorporated by reference. Definitions that are contained in text incorporated by reference are excluded to the extent that they contradict definitions in this disclosure.

The present invention is further illustrated by the following examples, which should not be considered as limiting in any way.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.
Chemicals, Device Fabrication, and Imaging
Chemicals The anionic fluorophore BODIPY$^{2-}$ 4,4-difluoro-1,3,5,7,8-pentamethyl-4-bora-3a,4a-diaza-S-indacene-2-6-disulfonic acid was obtained from Molecular Probes (Eugene, OR). Texas Red dye-linked bovine serum albumin ("Texas Red") was also used as a fluorophore. Sodium phosphate buffer at pH 7.3 or Tris buffer at pH 8.0 was used to fill the auxiliary channel and the dispersed droplet phase at the concentration indicated in each Example. For the continuous phase, heavy mineral oil with 0.1 w/w % of Triton™-X100 from Dow Chemical and 2 w/w % or 3 w/w % ABIL® EM 90 from Evonik (Essen, Germany) was used. Nafion™ perfluorinated resin, 10 wt-% solution in lower aliphatic alcohols, was purchased from Sigma-Aldrich (St. Louis, MO). Cell permeant Rhod-2, tripotassium salt, was used as a calcium indicator. OptiPrep™ was obtained from Sigma Aldrich (St. Louis, MO). MDA-MB-231 human breast cancer cell line was used in Examples 8-10. The cancer cell was stained with Calcein AM green fluorescence dye from Fisher Scientific (Waltham, MA).

All other solutions were made with reagent grade chemicals from Fisher Scientific (Waltham, MA) and diluted with 18.2 MΩ·cm double deionized ("d.d.i.") water using a Sartorius Arium Pro (Gottingen, Germany) before use to desired concentration.

SU-8-2025 and SU-8 2050 negative photoresist from Microchem Corp. (Westborough, MD), silicon ("Si") substrate, and polydimethylsiloxane ("PDMS"), Sylgard 184 elastomer kit from Dow Corning Corp. (Midland, MI) were used for device fabrication. The 02 plasma was conducted via a 60 W, PDC-001, from Harrick Plasma (Ithaca, NY).

99.95% platinum electrodes were purchased from Strem Chemicals (Newburyport, MD).
Device Fabrication The device was constructed from a glass substrate, onto which two parallel thin film Nafion membranes were patterned and aligned with an upper PDMS monolith that defined three independent microfluidic channels. The membranes were flow-patterned on the glass substrate as follows. First, as depicted in green in FIG. 3A, a PDMS monolith was cast-molded on a Si wafer patterned with SU-8 2025. The PDMS was imprinted with two channels spaced 300 µm apart measuring 6.0 mm long, 400 µm wide, and 25.0 µm tall with a 1.0 mm-diameter inlet and outlet. Second, a 25 mm×25 mm×1 mm glass slide was cleaned in an alkaline solution of NH$_4$OH:H$_2$O:H$_2$O$_2$, 1:1:1, at 60° C. for 10 minutes followed by rinsing with d.d.i. water, ethanol, drying with N$_2$, and a 60-second exposure to O$_2$ plasma. Third, the PDMS monolith was reversibly sealed to the glass slide. Nafion resin was pipetted on top of the inlet of each channel and then pulled through by suction applied to the outlet as depicted in FIG. 3B. Then, the glass slide was baked at 95° C. for 10 minutes on a hot plate to cure the Nafion as depicted in FIG. 3C. While curing, the Nafion shrunk to its final thickness of 2-8 The PDMS used to pattern the membranes was peeled away leaving cured Nafion on the slide glass.

Separately, as depicted in orange in FIG. 3A, a PDMS monolith defining three microchannels was fabricated by soft lithography from an SU-8 2050 patterned Si wafer. The central main microchannel was 10.0 mm long, 500 µm wide, and 50.0 µm tall spanning a 1.0 mm diameter inlet and outlet. The two flanking auxiliary channels were separated from the main channel by 250 µm and were 5.0 mm long, 500 µm wide, and 50.0 µm tall with 4.0 mm diameter reservoirs at each end. This PDMS monolith was exposed to an 02 plasma for 60 seconds. Immediately after plasma treatment, these three microchannels were aligned on top of the membranes as depicted in FIG. 3D and baked at 95° C. for 10 minutes in an oven to improve bonding. Note that the channels were aligned parallel to the membranes and centered on them such that each membrane spanned the wall between an auxiliary channel and the main channel. Finally, the main channel was filled with the oil phase, and the auxiliary channels were filled with an aqueous electrolyte (e.g. phosphate buffer) with concentration matched to that of the droplets described in each Example.

Droplet Generation

For some Examples, a microfluidic droplet generator was used to form droplets with volumes ranging from approximately 2.5 to 25.0 nL depending on the input flow rates of the two phases. The volumetric flow rates were controlled using the syringe pump Pump 11 Pico Plus Elite from Harvard Apparatus (Holliston, MA). Droplets were collected in 1.0 mL vials before recovery and injection via 1.0 mm outside diameter ("OD") tubing into the device employed for enrichment.

For the Examples utilizing 1 nL droplets, droplet generation employs a device that consists of two serpentine channels emerging from respective inlet reservoirs containing continuous and dispersed phases. These two channels converge at a T-junction and generate nanoliter-scale droplets.

Device Use

The flow of the droplet/oil emulsion into the main channel was modulated by controlling the inlet pressure with a syringe to achieve the average linear velocities indicated in the Example. A driving voltage was applied across the device using the DC power supply Model 6487, Keithley Picoammeter, from Tektronix Inc. (Beaverton, OR) connected to platinum wires positioned in both reservoirs of each the "upper" (V+) and "lower" (Gnd) auxiliary channels. Droplets evaluated in these Examples are top-down images of the droplet. The auxiliary channel with the voltage applied is oriented to be in the top of the image, therefore labeled or described as "upper" or "top" or "V+" and the grounded auxiliary channel is oriented in the bottom of the image, and therefore described or labeled as "lower" or "bottom" or "GND," The voltages employed for each individual trial are indicated in the Example.

Fluorescence Measurement and Image Processing

All fluorescence measurements were performed using an Eclipse Ti-S inverted fluorescence microscope from Nikon Industries (New York, NY) equipped with an Orca-4.0 digital camera from Hamamatsu Corp. (Bridgewater, NJ). All images were obtained using NISElements 4.6 software from Nikon. Videos were recorded with a frame rate of 5 fps, and cell lysis videos were recorded at a frame rate of 15 fps. In the case of in-droplet separation of two fluorescent tracer dyes, individual images were taken at the times indicated in each Example. Enrichment factor was calculated as the fold increase in concentration of the fluorescent tracer (e.g. $BODIPY^{2-}$) as determined by comparing the maximum fluorescence to that obtained prior to the application of the driving voltage.

The recorded video files were converted into sequential images using ImageJ 1.51. Further image processing was carried out in MATLAB R2017b, or MATLAB R2019b. To define the projected area of the entire droplet and the IDZ, the sequential images were converted to gray scale. Next, image opening and closing were performed on the first image, at t=0 seconds, to determine a droplet boundary that excluded neighboring droplets. From a binarized image, the equivalent diameter was measured, and the droplet mask was created enabling one-by-one image processing on a droplet. The average fluorescence intensity in a droplet, before concentration polarization, was obtained by dividing the total intensity by the area of the droplet. For the rest of the frames, t>0 seconds, the maximum intensity was divided by the initial average intensity to obtain the EF. For Example 5, local EF was defined by dividing the instantaneous intensity at each pixel by its initial intensity, at t=0 seconds. Then, the value was window averaged to minimize the contribution of the pixel noise to EF. The IDZ was defined as all the pixels in a droplet having an intensity less than 50% of the initial average intensity. To evaluate the normalized IDZ size, the IDZ area is defined by setting a threshold at one-half of the spatially averaged intensity within the droplet. Image pixels having intensities below this threshold were considered to be part of the IDZ area, which was then normalized to total droplet area. Mass conservation inside a droplet was confirmed by monitoring the total intensity of the droplet for each frame. For droplets evaluated under flowing conditions, the position of the center of the droplet was compared between frames to measure its instantaneous velocity.

Example 1

Standing Droplet Electrokinetics

In this Example, the electrokinetics of charged species in standing droplets was investigated.

Figure 5A:
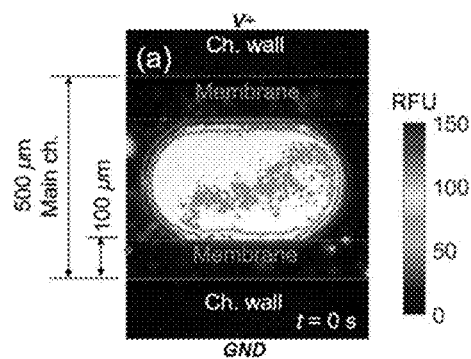
FIG. 5A is a fluorescence micrograph showing the temporal evolution of the distribution of an anionic fluorescent tracer at t=0 seconds after initiation of an applied voltage of V+=15.0 V. Prior to application of the voltage, the droplet was comprised uniformly of 10.0 µM BODIPY$^{2-}$ in 10.0 mM phosphate buffer. Overlaid isometric contours are included to highlight the enriched area inside the droplet.
Figure 5B:
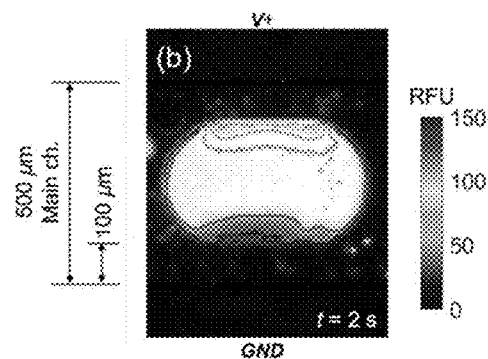
FIG. 5B is a fluorescence micrograph showing the temporal evolution of the distribution of an anionic fluorescent tracer at t=2 seconds after initiation of an applied voltage of V+=15.0 V. Prior to application of the voltage, the droplet was comprised uniformly of 10.0 µM BODIPY$^{2-}$ in 10.0 mM phosphate buffer. Overlaid isometric contours are included to highlight the enriched area inside the droplet.
Figure 5C:
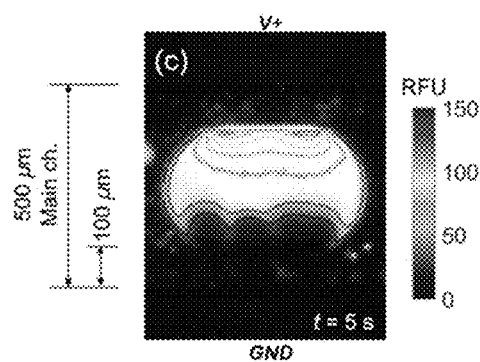
FIG. 5C is a fluorescence micrograph showing the temporal evolution of the distribution of an anionic fluorescent tracer at t=5 seconds after initiation of an applied voltage of V+=15.0 V. Prior to application of the voltage, the droplet was comprised uniformly of 10.0 μM BODIPY$^{2-}$ in 10.0 mM phosphate buffer. Overlaid isometric contours are included to highlight the enriched area inside the droplet.

The device used in this Example was prepared as described above. Droplets comprising 10.0 mM phosphate buffer and 10.0 μM $BODIPY^{2-}$, were inserted into the main channel. 15.0 V was applied to the reservoirs of the anodic auxiliary channel ("V+"), and ground to the cathodic auxiliary channel ("GND"). Once the voltage bias was applied, a gradient in the fluorescence intensity was observed to develop across the droplet as indicated in FIGS. 5A, 5B and 5C. FIG. 5A is at t=0 seconds and the images in FIGS. 5B and 5C are 2 and 5 seconds after application of the voltage, respectively. The concentration gradient results from cation selective ionic current through the membranes contacting the droplet, which leads to high concentration, the IEZ, adjacent to the anodic membrane and depletion, the IDZ, at the cathodic end demonstrating that there is ionic communication between the droplet and the membranes, which leads to concentration polarization. Without being limited to a particular theory, the results imply that ions are either transported across the oil layer, which surrounds the droplet, or the droplet wets the membrane. The latter mechanism is likely since the membrane is primed by being hydrated in the aqueous electrolyte prior to the experiment.

FIGS. 5A, 5B, and 5C illustrate the temporal evolution of the concentration profile in the ion depleted and enriched zones. Isometric contour lines are overlaid on top of the fluorescence images to aid in visualization. Two local maxima were developed at the ends of the line of contact between the droplet and the anodic membrane as depicted by the red lines in FIGS. 5B and 5C, where the electric field strength was expected to be greatest. The IDZ boundary developed an irregular shape due to the presence of fluid vortices as illustrated in FIG. 2 ("Fluidic instability") and depicted in FIG. 5C near the grounded auxiliary channel. Vortex flow causes the scalloped IDZ boundary depicted in FIG. 5C. This fluidic instability may be electro- and diffusio-osmosis driven, respectively, by the steep gradients in electric field strength and ion concentration found there. Collectively, these features of the concentration profile provide strong evidence of ICP as the underlying mechanism for enrichment.

Figure 6:
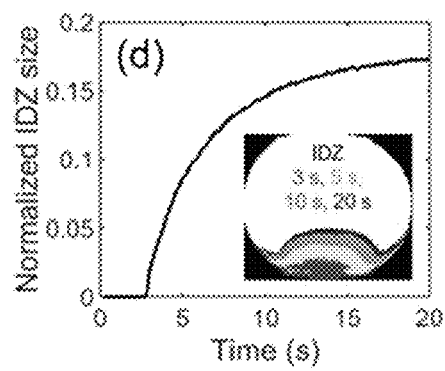
FIG. 6 shows IDZ size over time and IDZ area relative to the projected droplet area for a 2.5 nL stationary droplet under an applied voltage of 4.0 V. Prior to application of the voltage, the droplet was comprised uniformly of 10.0 μM BODIPY$^{2-}$ in 10.0 mM phosphate buffer.
Figure 7:
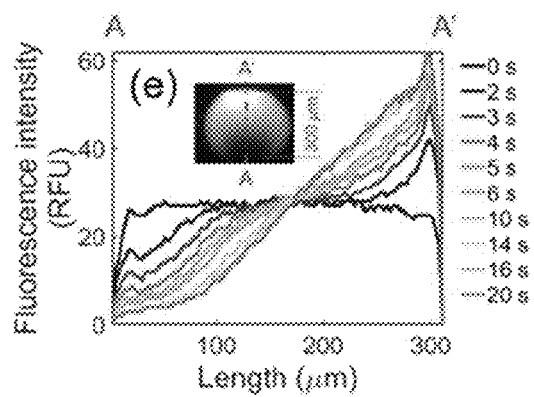
FIG. 7 shows fluorescence intensity for various times along the droplet centerline for a 2.5 nL stationary droplet under an applied voltage of 4.0 V. Prior to application of the voltage, the droplet was comprised uniformly of 10.0 μM BODIPY$^{2-}$ in 10.0 mM phosphate buffer.
Figure 8:
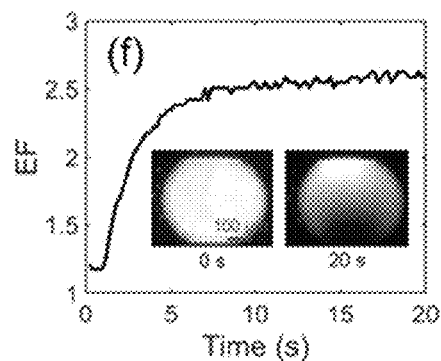
FIG. 8 shows the evolution of enrichment factor ("EF") over time for a 2.5 nL stationary droplet under an applied voltage of 4.0 V. Prior to application of the voltage, the droplet was comprised uniformly of 10.0 μM BODIPY$^{2-}$ in 10.0 mM phosphate buffer.
Figure 9A:
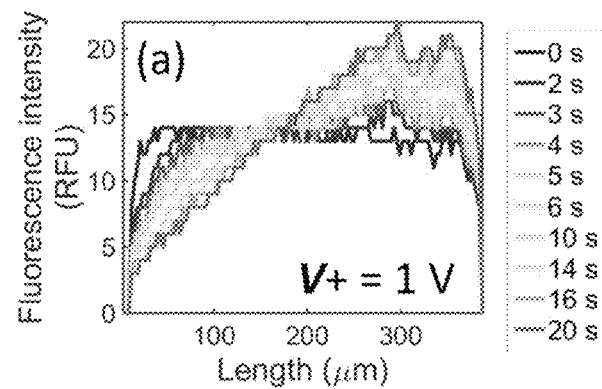
FIG. 9A depicts the fluorescence intensity profile along a droplet centerline of a 22.3 nL droplet containing 1.0 mM phosphate buffer and 10.0 μM BODIPY$^{2-}$ with an applied voltage bias of 1.0 V.
Figure 9B:
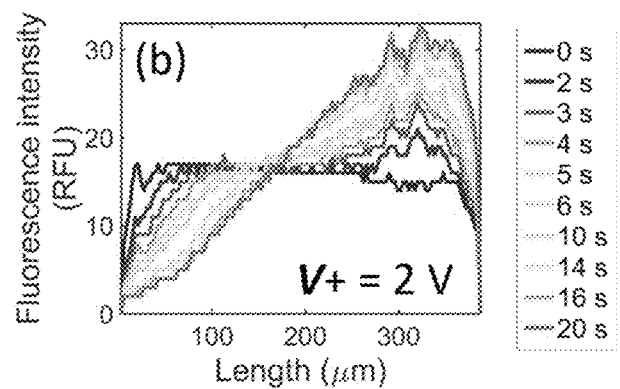
FIG. 9B depicts the fluorescence intensity profile along a droplet centerline of a 22.3 nL droplet containing 1.0 mM phosphate buffer and 10.0 μM BODIPY$^{2-}$ with an applied voltage bias of 2.0 V.
Figure 9C:
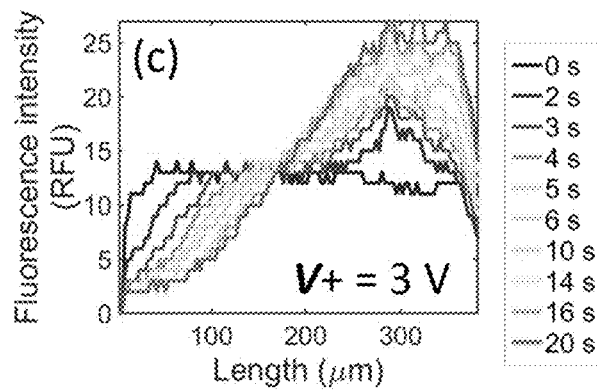
FIG. 9C depicts the fluorescence intensity profile along a droplet centerline of a 22.3 nL droplet containing 1.0 mM phosphate buffer and 10.0 μM BODIPY$^{2-}$ with an applied voltage bias of 3.0 V.
Figure 9D:
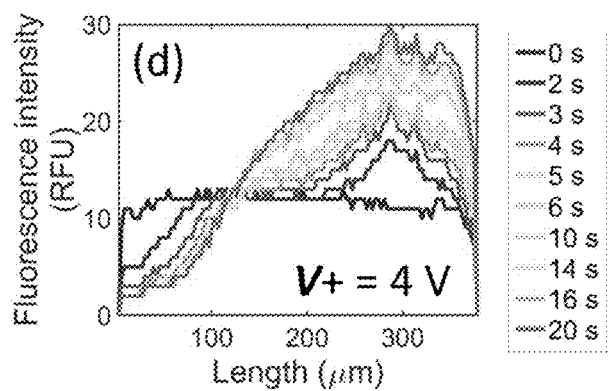
FIG. 9D depicts the fluorescence intensity profile along a droplet centerline of a 22.3 nL droplet containing 1.0 mM phosphate buffer and 10.0 μM BODIPY$^{2-}$ with an applied voltage bias of 4.0 V.
Figure 9E:
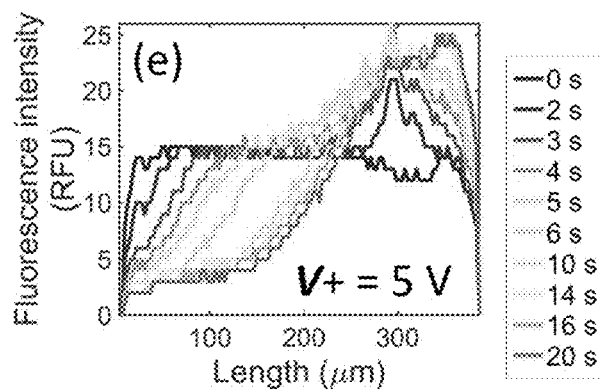
FIG. 9E depicts the fluorescence intensity profile along a droplet centerline of a 22.3 nL droplet containing 1.0 mM phosphate buffer and 10.0 μM BODIPY$^{2-}$ with an applied voltage bias of 5.0 V.
Figure 10A:
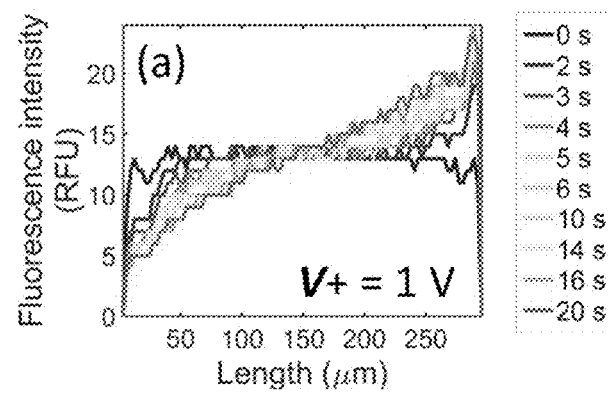
FIG. 10A depicts the fluorescence intensity profile along a droplet centerline of a 3.9 nL droplet containing 1.0 mM phosphate buffer and 10.0 μM BODIPY$^{2-}$ with an applied voltage bias of 1.0 V.
Figure 10B:
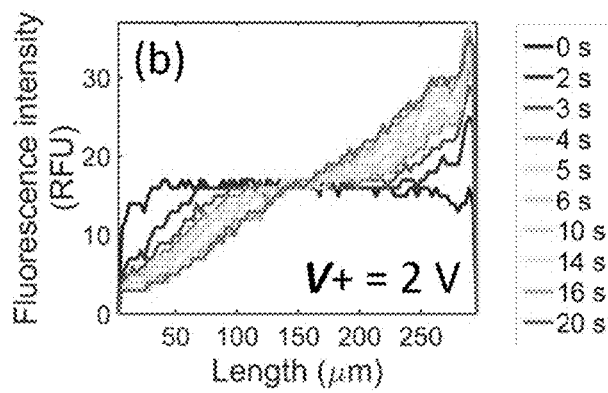
FIG. 10B depicts the fluorescence intensity profile along a droplet centerline of a 3.9 nL droplet containing 1.0 mM phosphate buffer and 10.0 μM BODIPY$^{2-}$ with an applied voltage bias of 2.0 V.
Figure 10C:
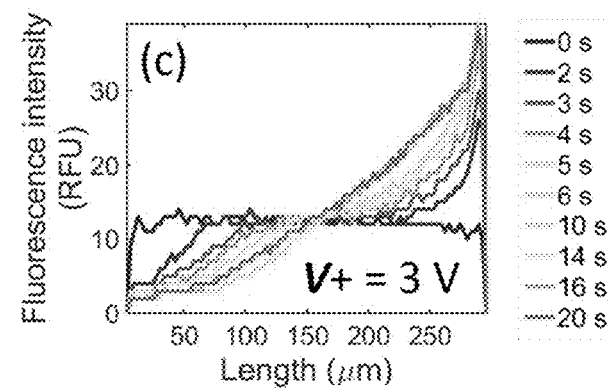
FIG. 10C depicts the fluorescence intensity profile along a droplet centerline of a 3.9 nL droplet containing 1.0 mM phosphate buffer and 10.0 μM BODIPY$^{2-}$ with an applied voltage bias of 3.0 V.
Figure 10D:
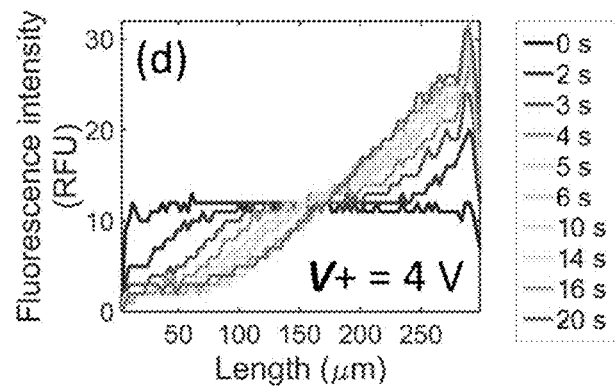
FIG. 10D depicts the fluorescence intensity profile along a droplet centerline of a 3.9 nL droplet containing 1.0 mM phosphate buffer and 10.0 μM BODIPY$^{2-}$ with an applied voltage bias of 4.0 V.
Figure 10E:
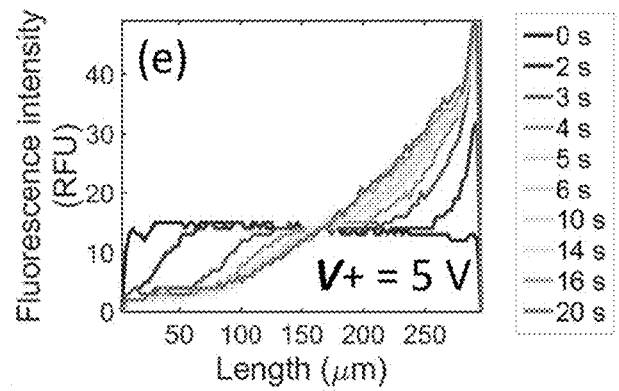
FIG. 10E depicts the fluorescence intensity profile along a droplet centerline of a 3.9 nL droplet containing 1.0 mM phosphate buffer and 10.0 μM BODIPY$^{2-}$ with an applied voltage bias of 5.0 V.

The temporal evolution of ICP in a standing droplet is further characterized by plotting the normalized IDZ size as shown in FIG. 6, concentration profile as shown in FIG. 7 and EF as shown in FIG. 8. The volume of the standing droplet for FIGS. 6, 7, and 8 is 2.5 nL and the applied voltage is 4.0 V. FIG. 6 shows that the normalized IDZ size increased rapidly within the first 10 seconds following initiation of a voltage bias and then approached an asymptote at 0.17, 17% of the droplet, at 20 seconds. The inset of FIG. 6 further illustrates the growth of the IDZ in the droplet over time as indicated by the shaded region. FIG. 7 shows the evolution of the intensity profile along the droplet centerline, which is parallel to the electric field. A concentration gradient develops rapidly and then approaches a steady state at time greater than 10 seconds, exhibiting a distinctive characteristic of droplet enrichment. This behavior contrasts that of conventional enrichment by ICP in a single phase, where a shockwave-like concentration gradient propagates upstream without interruption. The spatially constrained ICP presented here allows for manipulation of charged compounds in an individual droplet without disturbing the continuous phase (the oil) or other droplets. Another notable feature of the concentration profile is that it is nearly linear and, under the conditions of relatively low voltage, extends across the entire width of the droplet, which leads to just over 2.5-fold enrichment.

Figure 11A:
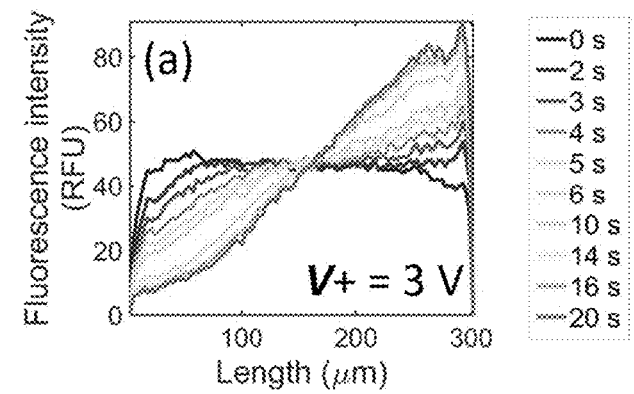
FIG. 11A depicts the fluorescence intensity profile along a droplet centerline of a 6.4 nL droplet containing 10.0 mM phosphate buffer and 10.0 μM BODIPY$^{2-}$ with an applied voltage bias of 3.0 V.
Figure 11B:
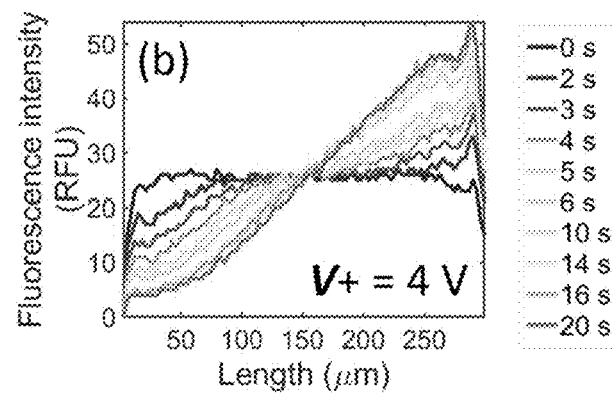
FIG. 11B depicts the fluorescence intensity profile along a droplet centerline of a 6.4 nL droplet containing 10.0 mM phosphate buffer and 10.0 μM BODIPY$^{2-}$ with an applied voltage bias of 4.0 V.
Figure 11C:
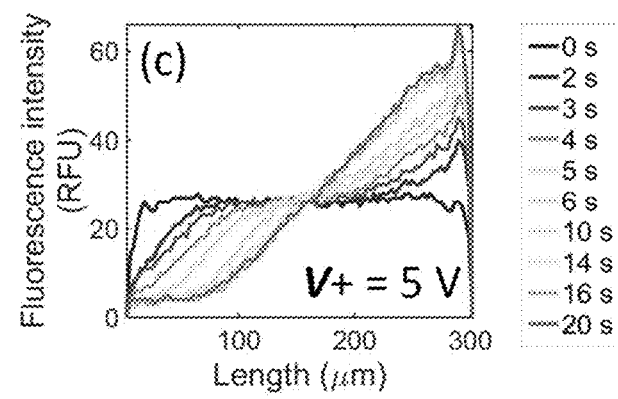
FIG. 11C depicts the fluorescence intensity profile along a droplet centerline of a 6.4 nL droplet containing 10.0 mM phosphate buffer and 10.0 μM BODIPY$^{2-}$ with an applied voltage bias of 5.0 V.
Figure 11D:
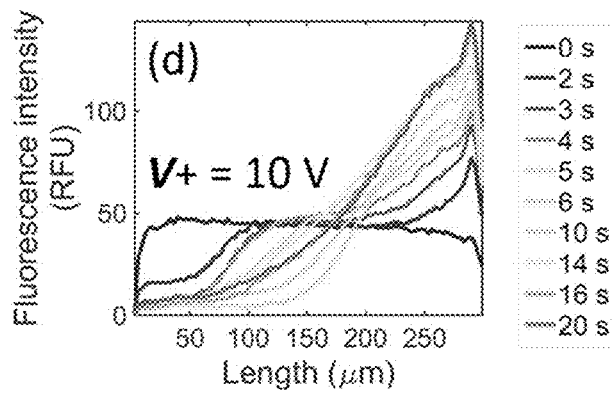
FIG. 11D depicts the fluorescence intensity profile along a droplet centerline of a 6.4 nL droplet containing 10.0 mM phosphate buffer and 10.0 μM BODIPY$^{2-}$ with an applied voltage bias of 10.0 V.
Figure 11E:
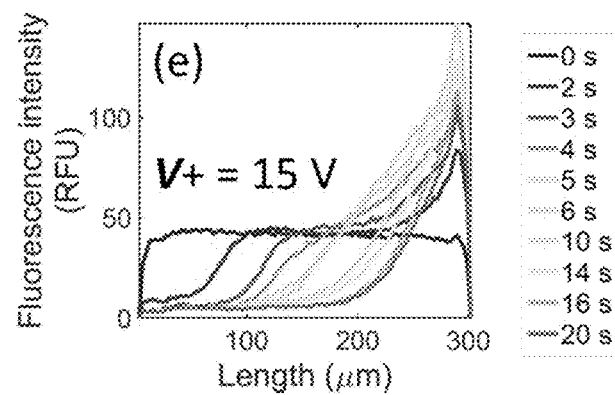
FIG. 11E depicts the fluorescence intensity profile along a droplet centerline of a 6.4 nL droplet containing 10.0 mM phosphate buffer and 10.0 μM BODIPY$^{2-}$ with an applied voltage bias of 15.0 V.
Figure 12A:
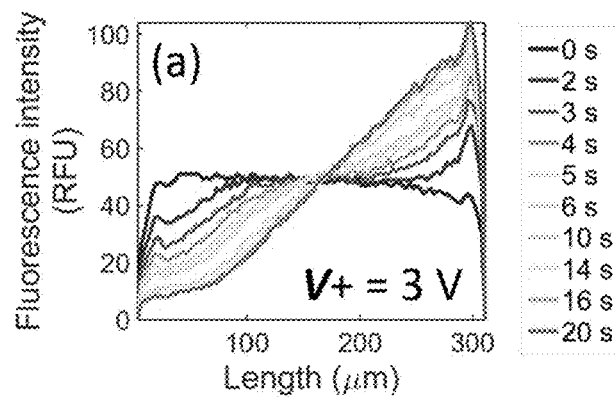
FIG. 12A depicts the fluorescence intensity profile along a droplet centerline of a 4.6 nL droplet containing 10.0 mM phosphate buffer and 10.0 μM BODIPY$^{2-}$ with an applied voltage bias of 3.0 V.
Figure 12B:
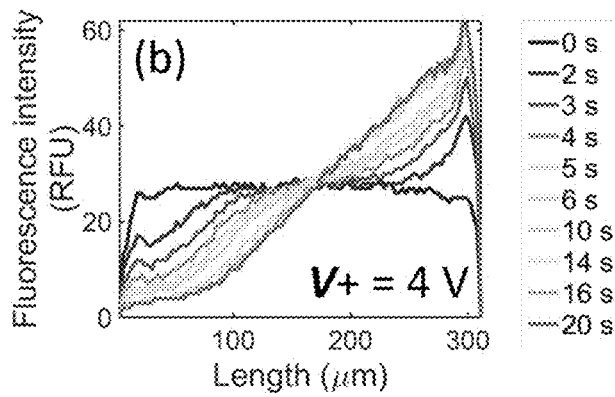
FIG. 12B depicts the fluorescence intensity profile along a droplet centerline of a 4.6 nL droplet containing 10.0 mM phosphate buffer and 10.0 μM BODIPY$^{2-}$ with an applied voltage bias of 4.0 V.
Figure 12C:
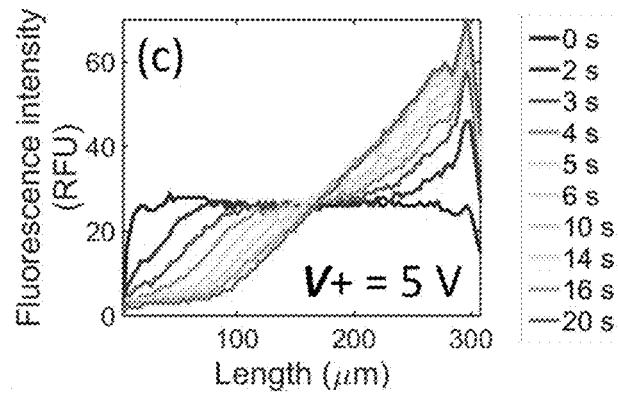
FIG. 12C depicts the fluorescence intensity profile along a droplet centerline of a 4.6 nL droplet containing 10.0 mM phosphate buffer and 10.0 μM BODIPY$^{2-}$ with an applied voltage bias of 5.0 V.
Figure 12D:
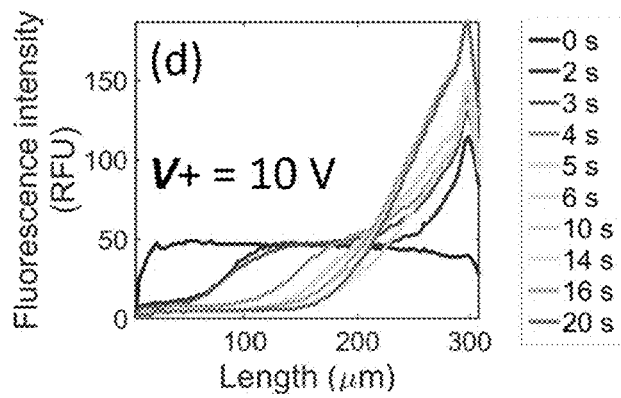
FIG. 12D depicts the fluorescence intensity profile along a droplet centerline of a 4.6 nL droplet containing 10.0 mM phosphate buffer and 10.0 μM BODIPY$^{2-}$ with an applied voltage bias of 10.0 V.
Figure 12E:
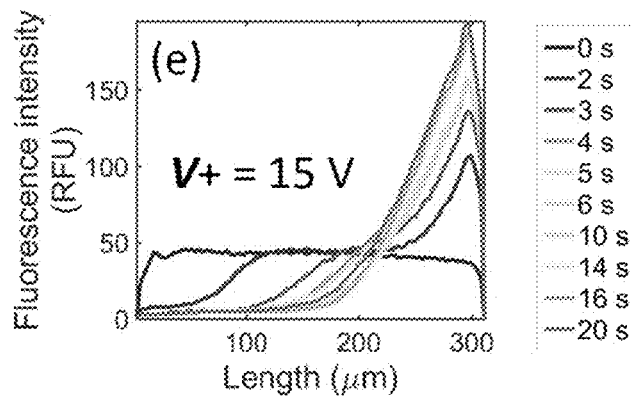
FIG. 12E depicts the fluorescence intensity profile along a droplet centerline of a 4.6 nL droplet containing 10.0 mM phosphate buffer and 10.0 μM BODIPY$^{2-}$ with an applied voltage bias of 15.0 V.

Results obtained at higher voltages display steeper gradients and an IDZ boundary extending past the equator of the droplet, thereby enabling greater enrichment. This is depicted in FIGS. 9, 10, 12, and 13. FIGS. 9A through 9E show the fluorescence intensity profile along the droplet centerline of a 22.3 nL droplet containing 1.0 mM phosphate buffer and 10.0 µM BODIPY$^{2-}$ with an applied voltage bias of 1.0 V, 2.0 V, 3.0 V, 4.0 V, and 5.0 V respectively. Similarly, FIGS. 10A through 10E show the fluorescence intensity profile along the droplet centerline of a 3.9 nL droplet containing 1.0 mM phosphate buffer and 10.0 µM BODIPY$^{2-}$ with an applied voltage bias of 1.0 V, 2.0 V, 3.0 V, 4.0 V, and 5.0 V respectively. FIGS. 11A through 11E depict the fluorescence intensity profile along the droplet centerline of a 6.4 nL droplet containing 10.0 mM phosphate buffer and 10.0 µM BODIPY$^{2-}$ with an applied voltage bias of 3.0 V, 4.0 V, 5.0 V, 10.0 V, and 15.0 V respectively, while FIGS. 12A through 12E show the fluorescence intensity profile along the droplet centerline of a 4.6 nL droplet containing 10.0 mM phosphate buffer and 10.0 µM BODIPY$^{2-}$ with an applied voltage bias of 3.0 V, 4.0 V, 5.0 V, 10.0 V, and 15.0 V respectively. The steeper gradients and an IDZ boundary extending past the equator of the droplet is especially clear at applied voltages of 10.0 V as shown in FIG. 11D and FIG. 12D and at applied voltages of 15.0 V as shown in FIGS. 11E and 12E.

FIG. 8 shows that EF increases rapidly over the first 5 seconds and then reaches its maximum value of 2.5 at t=10 seconds. Unlike conventional ICP-based enrichment in which electrostatic repulsion of a charged species, such as an analyte, from the IDZ is balanced by convection, in this case, there is not a continuous flux of this species from upstream, instead repulsion is balanced by geometric confinement. For this reason, isolation of species within a droplet presents both a disadvantage of limited enrichment, and an important advantage in many chemical and biological systems. First, there is often meaningful spatiotemporal variation in the composition of the input sample stream, such as when monitoring cell secretions or the effluent of chromatographic or electrophoretic separation. In such a case, enrichment prior to droplet encapsulation would lead to loss of information. Second, each droplet may contain distinct entities, such as individual cells or nanoparticles. Third, confinement is a key feature of certain processes, as in the formation of crystallites or nanoscale materials, processes which could be augmented by enrichment.

Example 2

Conservation of Mass in Droplets

In this Example, the integral of fluorescence intensity across the entire area of the droplet was monitored over time to verify conservation of the fluorophore in the droplet.

The device used in this Example was prepared as described above. The W/O interface and cation selective membrane isolate anionic analytes inside the droplet, allowing enrichment without loss of analyte. The variation in integrated fluorescence intensity across the droplet, $\delta_t$, was evaluated using Formula I wherein $I_t$, $I_0$, and $\Omega_D$ are the local intensity at time t, the local intensity at time t=0 seconds, and the projected area of the droplet in the image. Subscript i represents the pixel index.

$$\delta_t = \frac{\int_{\Omega_D} I_t \partial \Omega_D - \int_{\Omega_D} I_0 \partial \Omega_D}{\int_{\Omega_D} I_0 \partial \Omega_D} \approx \frac{\sum_{i \in \Omega_D} I_{t,i} - \sum_{i \in \Omega_D} I_{0,i}}{\sum_{i \in \Omega_D} I_{0,i}} \quad (I)$$

Figure 4A:
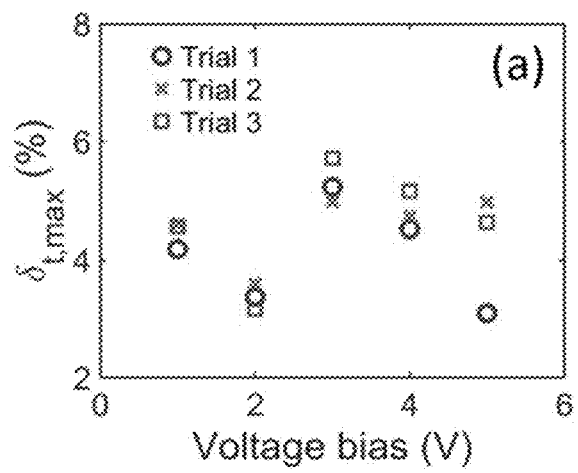
FIG. 4A shows the maximum percent change in integrated fluorescence during the enrichment of the contents of stationary droplets at several voltages for a 22.3 nL droplet comprising 10.0 µM BODIPY$^{2-}$ (4,4-Difluoro-1,3,5,7,8-pentamethyl-4-bora-3a,4a-diaza-s-indacene-2,6-disulfonic acid) in 1.0 mM phosphate buffer.
Figure 4B:
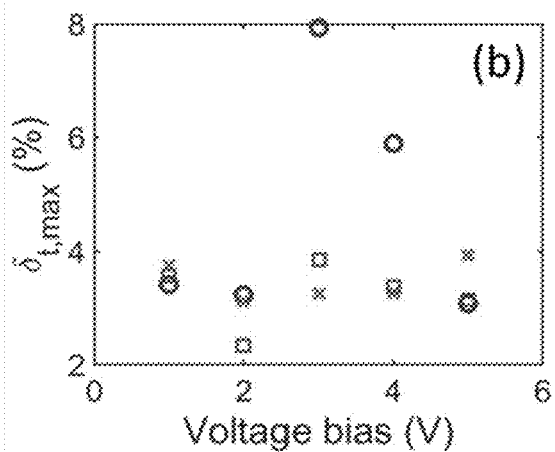
FIG. 4B shows the maximum percent change in integrated fluorescence during the enrichment of stationary droplets at several voltages for a 3.9 nL droplet comprising 10.0 µM BODIPY$^{2-}$ in 1.0 mM phosphate buffer.
Figure 4C:
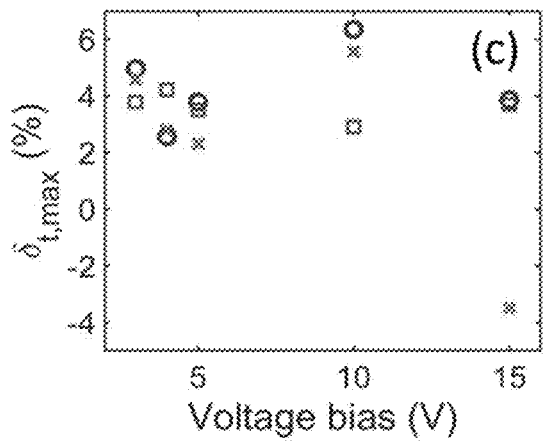
FIG. 4C shows the maximum percent change in integrated fluorescence during the enrichment of stationary droplets at several voltages for a 6.4 nL droplet comprising 10.0 µM BODIPY$^{2-}$ in 10.0 mM phosphate buffer.
Figure 4D:
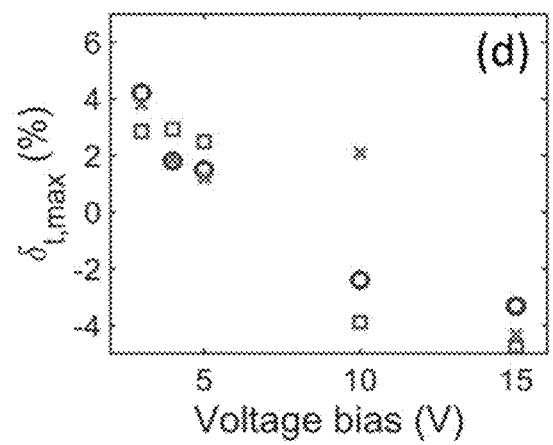
FIG. 4D shows the maximum percent change in integrated fluorescence during the enrichment of stationary droplets at several voltages for a 4.6 nL droplet comprising 10.0 µM BODIPY$^{2-}$ in 10.0 mM phosphate buffer.

FIGS. 4A, 4B, 4C, and 4D show the maximum $\delta_t$, expressed as a percentage, at several voltage biases, for several trials with stationary droplet. FIG. 4A shows the data for trials with 22.3 nL droplet and 1.0 mM phosphate buffer. FIG. 4B shows the data for trials with a 3.9 nL droplet and 1.0 mM phosphate buffer. FIG. 4C shows results for a 6.4 nL droplet and 10.0 phosphate buffer. FIG. 4D show the calculations using a 4.6 nL droplet and 10.0 mM phosphate buffer. The integral of fluorescence intensity across the entire area of the droplet was monitored over time to verify conservation of the fluorophore in the droplet. The maximum variation in this integral was calculated using Formula I for each droplet in all Examples included in this study, and the mean variation in these values was 3.8±0.3%. This result supports the conclusion that the observed concentration polarization is due to redistribution of the fluorophore within the droplet, and not leakage, photobleaching, or local shift in pH.

Example 3

Impact of Electrolyte Concentration, Applied Voltage, and Droplet Size

In this Example, the impact of electrolyte concentration, magnitude of the applied voltage bias, and droplet size on the concentration distribution of the anionic fluorophore in standing droplets was investigated.

The device used in this Example was prepared as described above. In this Example, two buffer concentrations, 1.0 mM and 10.0 mM phosphate buffer were evaluated, as well as droplets each with a distinct volume, over a range of voltages from 1.0 V to 15.0 V. At each condition, the ICP experiment was performed three times.

Figure 13A:
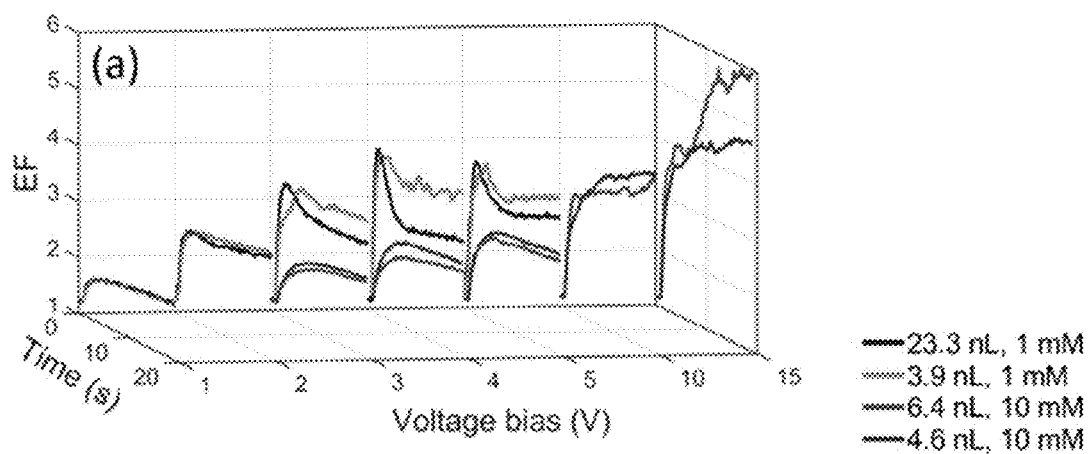
FIG. 13A is a plot of the enrichment factor (EF) over time and at several voltage biases for four distinct droplets having the volumes and buffer concentrations indicated.
Figure 13B:
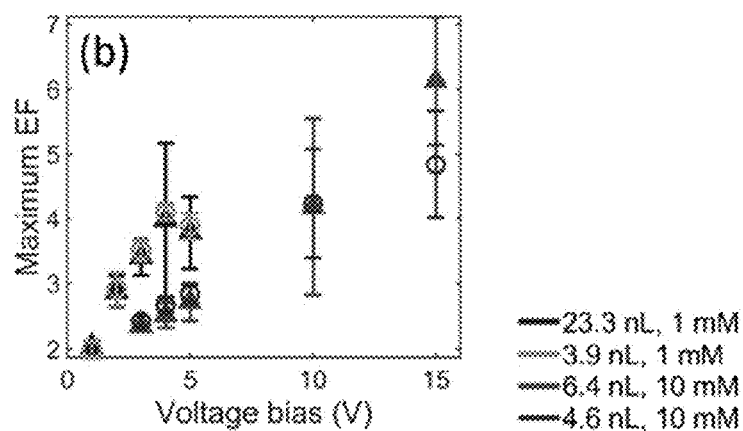
FIG. 13B is a plot of maximum EF as a function of the voltage bias applied for four distinct droplets having the volumes and buffer concentrations indicated. Error bars show the 95% confidence level.

FIG. 13A shows the temporal evolution of EF plotted as an ensemble average for each trial. In all cases, there is an initial rapid increase in EF from t=0 to 5 seconds, which then approaches a limiting value. The limiting EF and enrichment rate are positively correlated to voltage bias and negatively correlated to ionic strength. In FIG. 13B, the maximum EF, plotted as a function of voltage bias for each set of conditions, follows similar trends.

Without being limited to a particular mechanism or theory, the limit of enrichment, in a single phase, may be attributed to two distinct mechanisms. In the electrokinetic limit, an electric field gradient is defined by the dominant electrolyte species, and charged species in low abundance are focused by counterbalancing convection and electromigration at a specific electric field strength. In this scenario, having a high electrolyte concentration compared to that of the compounds to be enriched is key to achieving high EF because when their concentration approaches that of the electrolyte, the electric field gradient is locally damped. This phenomenon defines the electrokinetic limit. In an alternative mechanism, the limit is defined by the role that the enriched compound plays in maintaining electroneutrality (the "NT limit"). In this case, the charged compound carries a significant fraction of the ionic current. This fraction is increased at lower electrolyte concentration, which leads to a higher limiting EF. The negative correlation shown in FIG. 13A between the EF limit and electrolyte concentration implies that the in-droplet ICP reported here is governed by the NT mechanism.

Figure 14A:
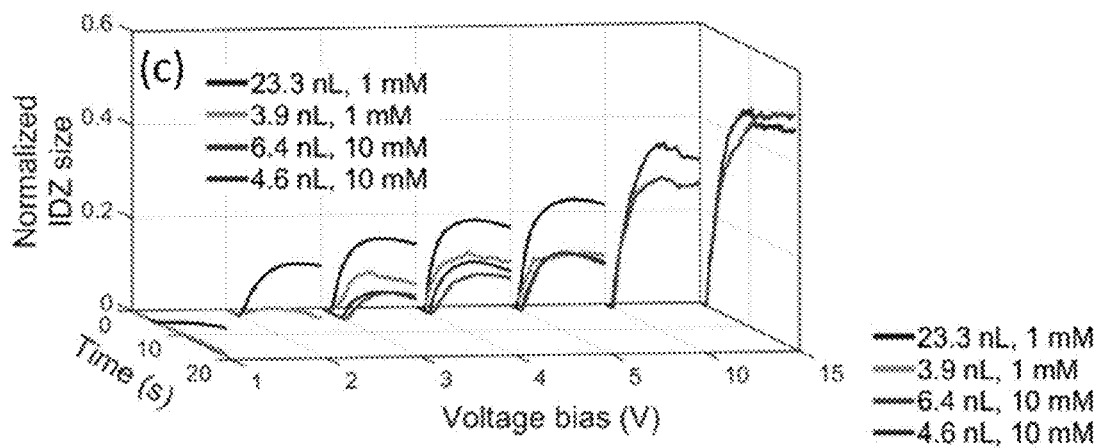
FIG. 14A is a plot of IDZ size normalized to droplet area for four distinct droplets having the volumes and buffer concentrations indicated.
Figure 14B:
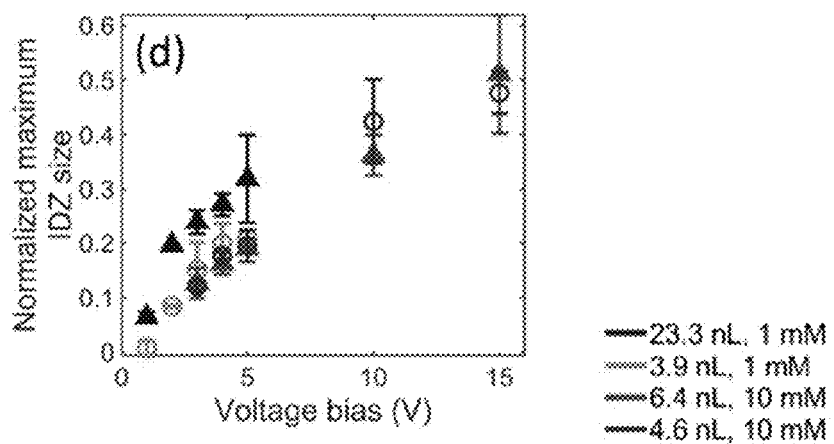
FIG. 14B is a plot of normalized IDZ size plotted for each voltage bias. Error bars show the 95% confidence level.

It is observed that in larger droplets, EF peaks early, for example at approximately 2.5 seconds for the 23.3 nL droplet and then decays to a lower steady value as shown in FIG. 13A. Without being limited to a particular theory, this disruption of the enrichment process is thought to be caused by the development of larger and more numerous vortices, leading to mixing, within a greater droplet volume. The onset of this fluidic instability is gradual, which explains the delayed decay in EF. As a measure of the efficiency of enrichment, the fraction of the droplet occupied by the IDZ was evaluated. FIGS. 14A and 14B show the projected area of the IDZ normalized to that of the entire droplet. By comparing IDZ size to EF for matched droplets, it is apparent that a larger IDZ corresponds to higher EF, except in the largest droplet, 23.3 nL, which implies that the efficiency of ICP is diminished. The results of FIGS. 13A, 13B, 14A, and 14B suggest maximum enrichment in smaller droplets, under higher voltage, and at lower ionic strength.

Example 4

Continuous Flow Droplets

In this Example, the impact of pressure-driven flow on enrichment in droplets was evaluated.

Figure 15:
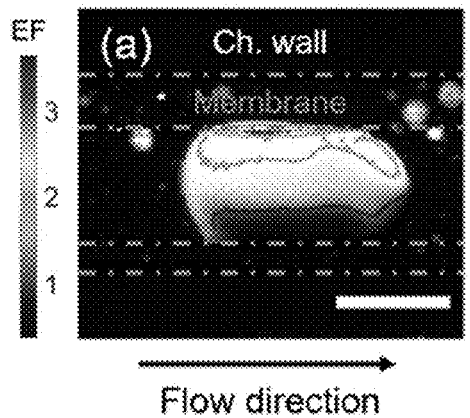
FIG. 15 is a fluorescence micrograph showing the distribution of an anionic fluorophore during enrichment at V+=10.0 V in droplets subjected to pressure driven flow at an average linear velocity of 210 μm/s. The scale bar length is 300 μm.
Figure 16:
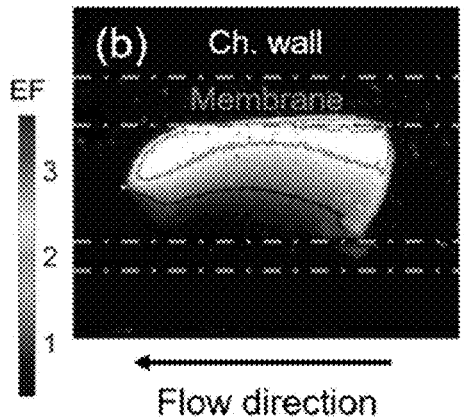
FIG. 16 is a fluorescence micrograph showing the distribution of an anionic fluorophore during enrichment at V+=10.0 V in droplets subjected to pressure driven flow at an average linear velocity of 241 μm/s.

The device used in this Example was prepared as described above. In this Example, droplets comprising 10.0 µM BODIPY$^{2-}$ in 1.0 mM phosphate buffer were flowed into the main channel at an average linear velocity of 210 µm/s from left to right as indicated in FIG. 15 and at an average linear velocity of 241 µm/s from right to left as indicated in FIG. 16. Then a voltage bias of 10.0 V was applied. The fluorescence micrograph in FIG. 15 was obtained at t=5 seconds and the fluorescence micrograph in FIG. 16 was obtained at t=9 seconds.

From the images in FIG. 15 and FIG. 16, it is apparent that the IDZ is distorted by the fluid flow and becomes asymmetrical. However, there is no gross mixing of the contents. This lack of mixing between the upper and lower halves can be attributed to known fluidic patterns that develop in flowing droplets; separate circulating flows develop in each half. This result confirms that enrichment can be maintained during flow.

Figure 17:
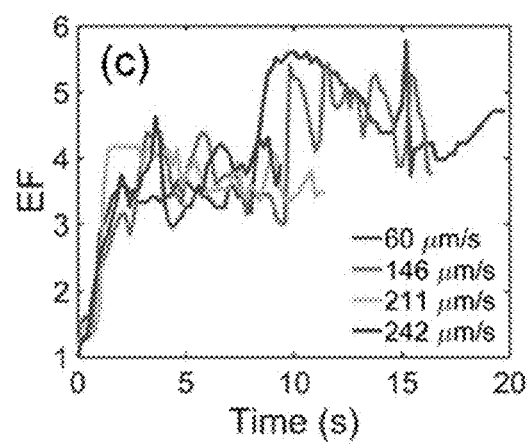
FIG. 17 is a plot of EF as a function of time at four distinct droplet velocities for a droplet comprising 10.0 μM BODIPY$^{2-}$ in 1.0 mM phosphate buffer during enrichment at V+=10.0 V.

FIG. 17 shows temporal evolution of EF observed at several fluid velocities. The maximum EFs were 3- to 5-fold, which is comparable to those obtained under similar conditions in stationary droplets as shown in FIG. 13A by the 4.6 nL droplet at 10.0 V, which supports the conclusion that mixing between the IDZ and IEZ is insignificant. Without being limited to a particular theory or mechanism, the fluctuation in EF as the droplet moves along the channel is attributed to irregularity of the surface of the cation selective membranes, leading to "hot" and "cold" spots, where the ionic current is higher and lower, respectively. This finding underscores the importance of reliable methods for fabricating reproducible and uniform ion permselective structures for the advancement of in-droplet ICP.

Example 5

In-Droplet Separation of Multiple Charged Species

In this Example, the ability of in-droplet ICP to accomplish separation of multiple charged compounds having distinct electrophoretic mobilities was investigated.

Figure 18:
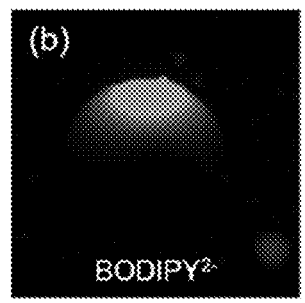
FIG. 18 is a fluorescence image showing the distribution of the green tracer BODIPY$^{2-}$ in a stationary droplet under applied voltage of 10.0 V.
Figure 19:
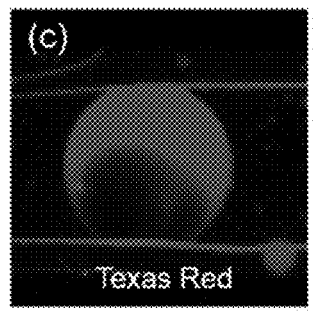
FIG. 19 is a fluorescence image showing the distribution of the red tracer Texas Red in a stationary droplet under applied voltage of 10.0 V.
Figure 20:
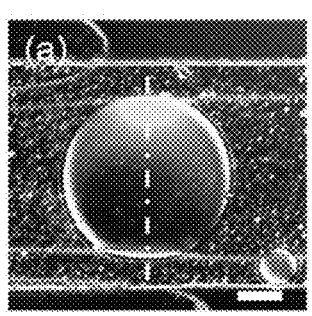
FIG. 20 is an overlaid image of brightfield differential interference contrast of a droplet with red and green fluorescence under an applied voltage of 10.0 V. The scale bar is 100 μm.

The device used in this Example was prepared as described above. In this Example, stationary droplets comprising 10.0 µM BODIPY$^{2-}$, 10 µM Texas Red, and 10 mM phosphate buffer were subjected to V+=10.0 V. Images of green and red fluorescence were obtained after 10 seconds as shown in FIG. 18 and FIG. 19 respectively. An overlay of the brightfield images of each droplet with red and green fluorescence in FIG. 20 show three distinct regions. There is depletion of both dyes near the bottom, cathodic end. There is a region of red dye only in the middle, and a region of both dyes together at the top, anodic end. This partial separation is linked to a greater degree of confinement for the higher mobility species due to relatively stronger migration away from the IDZ.

Figure 21:
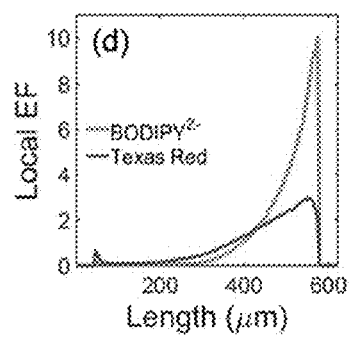
FIG. 21 is a plot of the local EF for each of the two tracers along the droplet cutline depicted in FIG. 16.
Figure 22:
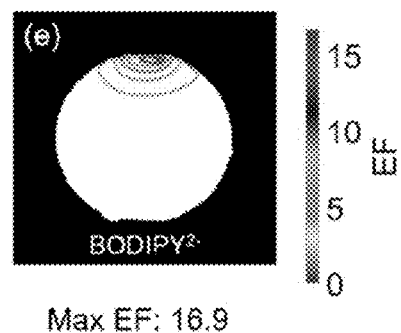
FIG. 22 depicts contour lines that map the distribution of tracer BODIPY$^{2-}$ as a function of local EF in a stationary droplet under applied voltage of 10.0 V.
Figure 23:
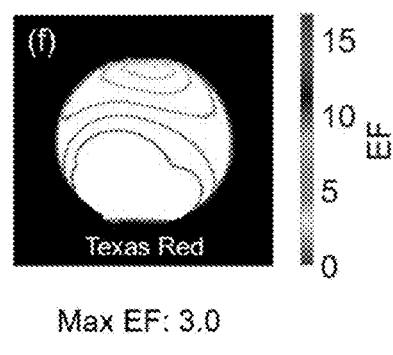
FIG. 23 depicts contour lines that map the distribution of tracer Texas Red as a function of local EF in a stationary droplet under applied voltage of 10.0 V

Plots of the local "fold" enrichment for each dye along the droplet centerline are shown in FIGS. 21, 22 and 23 and provide a more quantitative view of the concentration profiles. For both tracers, the highest local enrichment factor was found near the anodic membrane. The peak EF of BODIPY$^{2-}$ was 5 times larger than that for Texas Red, and the concentration gradient was steeper as shown in FIG. 21. From the separate images of BODIPY$^{2-}$ in FIG. 18 and Texas Red in FIG. 19 and the corresponding contour plots in FIG. 22 and FIG. 23, it is clear that there are different tiers of tracer enrichment. The separation of the tracers is more distinct when the radial distribution is considered. Finally, the penetration of Texas Red into the IDZ as indicated by the "fingers" of dye as seen in FIG. 19 demonstrates the mobility dependence of the instability. The practical implication of this finding is that low mobility compounds will undergo less efficient enrichment.

Electrokinetic separation in droplets promises to enable single-color ratiometric methods, such as mobility-shift assays, for more than one charged species. This enables processes such as fractionation prior to droplet splitting.

Example 6

Electrokinetically Driven Cation Exchange

In this Example, cation injection into droplets from the anodic auxiliary channel via the permselective membrane was demonstrated.

Figure 24:
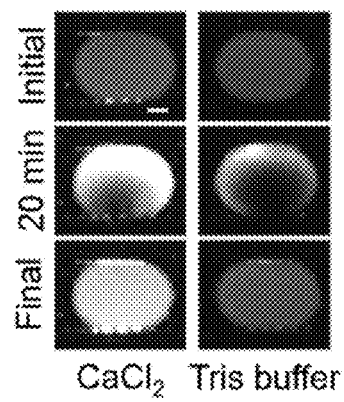
FIG. 24 shows droplet images obtained before ("Initial"), at time t=20 minutes ("20 min"), and 5 minutes after ("Final") applying a voltage bias for 30 minutes in the presence ("CaCl$_2$") and absence ("Tris buffer") of Ca$^{2+}$ in the anodic auxiliary channel.

The device used in this Example was prepared as described above. In this Example, stationary droplets comprising 10.0 µM calcium indicator dye Rhod-2 and 10.0 mM Tris buffer were evaluated, with variations in the electrolyte solution in the anodic auxiliary channel. In the first trial, the anodic auxiliary channel contained 10.0 mM Tris buffer. In the second trial, the anodic auxiliary channel contained 10.0 mM CaCl$_2$). FIG. 24 shows droplet images before ("Initial"), at time t=20 minutes ("20 min"), and 5 minutes after ("Final") applying a voltage bias of 5.0 V for 30 minutes.

Figure 27:
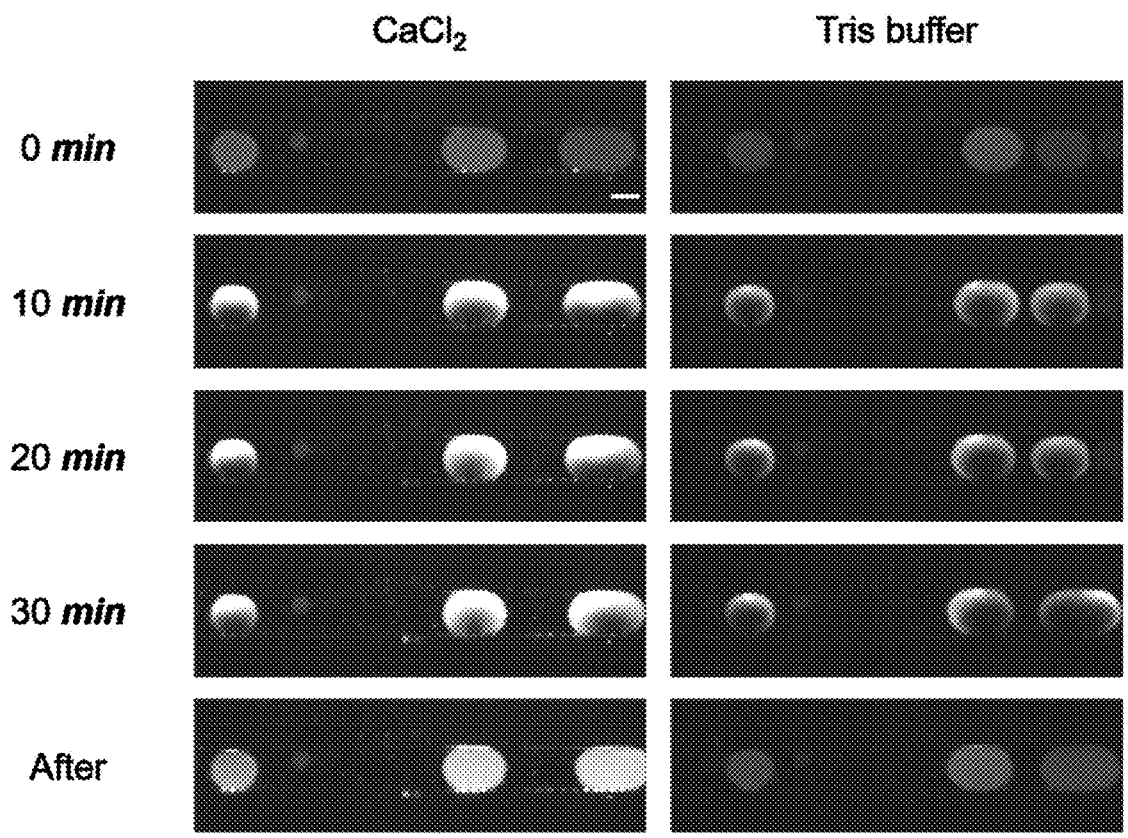
FIG. 27 shows droplet images obtained before ("0 min") and at time t=10 minutes ("10 min"), time t=20 minutes ("20 min"), time t=30 minutes ("30 min") after applying a voltage of 10.0 V, and 5 minutes after the voltage bias is removed ("After") of trials in the presence ("CaCl$_2$") and absence ("Tris buffer") of Ca$^{2+}$ in the anodic auxiliary channel.

In both trials, upon application of V+=5.0 V, the calcium indicator was enriched at the anodic membrane and depleted at the cathodic membrane as shown in FIG. 24 in the images labeled "20 min". After 30 min of operation, with Tris buffer in the anodic auxiliary channel, the intensity of the calcium indicator was unchanged. This is shown by comparing the Initial and Final images in the "Tris buffer" column of FIG. 24. In contrast, in the presence of $CaCl_2$) in the auxiliary channel, the fluorescence of the calcium indicator increased, exhibited by the comparison of the Initial and Final images in the $CaCl_2$) column of FIG. 24. In FIG. 27 fluorescence images over a longer segment of the main channel show three droplets after 0, 10, 20, 30 minutes of application of a voltage bias of 5.0 V and then 5 minutes after the voltage bias is removed ("After"). These images demonstrate the transport of $Ca^{2+}$ from the auxiliary channel into the droplet. This injection of cations must be balanced by removal of an equivalent quantity of charge from the droplet via the cathodic membrane, and therefore, this method also provides a means for selective ion extraction from droplets. Distinct morphologies of the IDZ were observed in the two cases as shown in the center row of FIG. 27, which is attributed to altered mobility of the indicator between its bound and unbound states. Upon binding $Ca^{2+}$, the indicator decreases in net charge from $3^-$ to $1^-$, which results in a lower mobility and corresponding smaller IDZ size. These results are consistent with those observed during separation of species with distinct mobilities as depicted in FIG. 18 and FIG. 19.

Figure 25:
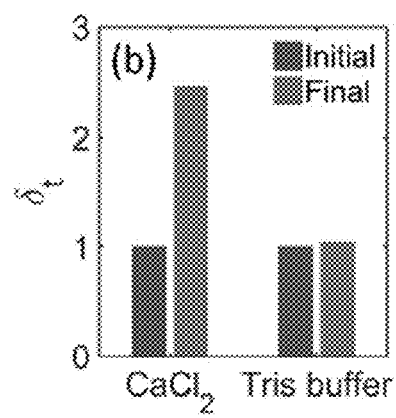
FIG. 25 shows normalized intensity variation Sc before and after trials in the presence ("CaCl$_2$") and absence ("Tris buffer") of Ca$^{2+}$ in the anodic auxiliary channel.
Figure 26:
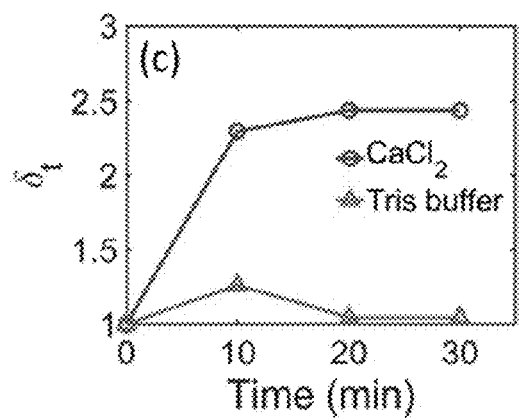
FIG. 26 is a plot of normalized intensity variation Sc over the duration of trials in the presence ("CaCl$_2$") and absence ("Tris buffer") of Ca$^{2+}$ in the anodic auxiliary channel.

The change in intensity due to $Ca^{2+}$ injection was quantified, and the normalized total intensities of the droplet $\delta_t$ are compared for the initial and final states of both cases in FIG. 25 and plotted in FIG. 26 as a function of time. After the injection of Ca', the indicator intensity increased by 2.5-fold, while there was no significant change in intensity in the absence of Ca'. The intensity approaches a limiting value in approximately 10 minutes, which is consistent with complete displacement of the initial Tris buffer content of the droplet, about 5 μC of ionic charge, at a rate of several nanoamperes of ionic current. This magnitude of current is typical for ICP at an ion selective membrane with a similar cross-sectional area in contact with an aqueous electrolyte solution. These results are significant because they demonstrate modification of droplet composition 'on the fly', without alteration of droplet volume. Further, the magnitude of the ion selective current, as controlled by the applied voltage and the serial resistances of the membranes and droplet, control the rate at which ionic charge is injected. Finally, the results provide further fundamental support for the mechanism illustrated by FIG. 2.

Example 7

Ion Concentration Polarization and Flow Field Simulation

In this Example, a computational simulation was performed to model the inner droplet domain. The cation and anion concentrations, electric potential and fluid flow were obtained by solving the Navier-Stokes ("NS") equation in Formula (II) and the coupled Poisson and Nernst-Planck ("PNP") equations in Formulas (III) and (IV) by finite element method. The PNP equations model the electromigration, and advection, of the ions in the droplet under imposed electric field. The NS equation models the motion dynamics of the droplet as it traverses the main channel. The coupling of between the NS and PNP equations ensures that ionic concentration impact on interfacial and bulk properties are accounted for.

$$\partial v/\partial t + v \cdot \nabla v = -1/\rho \nabla p + \upsilon \Delta v + g + \sigma \nabla \quad \text{(II)}$$

$$\nabla^2 \varphi = -\rho/\varepsilon \quad \text{(III)}$$

$$J = -D[\nabla c + zF/RTc\nabla \phi] + cv \quad \text{(IV)}$$

The droplet for the simulation has a width of 30 μm, notably smaller than the previous examples wherein the droplet had a width of about 300 μm.

Figure 28:
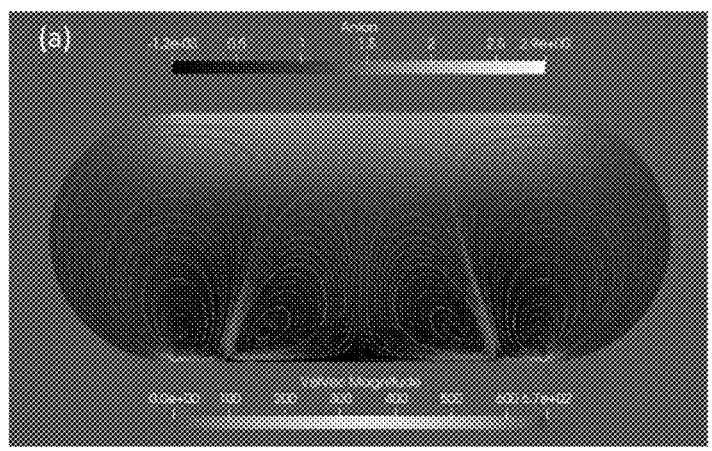
FIG. 28 is a simulation of anion concentration and flow streamlines in a 30 µm wide droplet with an applied voltage of 0.5 V.
Figure 29:
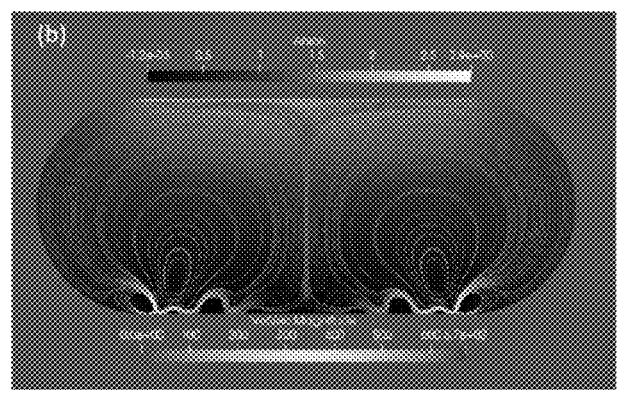
FIG. 29 is a simulation of anion concentration and flow streamlines in a 30 µm wide droplet with an applied voltage of 1.0 V.

Simulated anion concentration and flow streamlines are depicted in FIG. 28 with an applied voltage of 0.5 V and in FIG. 29 for an applied voltage of 1.0 V. As shown in these two figures, the anion concentration is high at the top where the droplet is in contact with the aniodic membrane and low at the bottom where the droplet is in contact with the cathodic membrane.

The depletion zone reaches to about the center line of the droplet. The interface between enrichment and depletion zone was distorted by fluid flow and high electric field at the membrane edge. The fluid flow was faster, and the streamline was more complex with higher applied voltage. These simulation results support the concentration contour and voltage dependency of the flow structure.

Example 8

In-Droplet Cell Lysis

In this Example, on-demand cell lysis via ICP was investigated.

The device used in this Example was prepared as described above, but with a smaller channel width of 50 μm. The droplets of this Example comprise 10% phosphate buffer, 17% OptiPrep, 10 μM Texas Red anionic tracer, and MDA-MB-231 human breast cancer cell line. The top and bottom auxiliary channels contain 200 mM Tris buffer. 50.0 V was applied to the anode at the reservoirs of the top auxiliary channel.

Figure 30A:
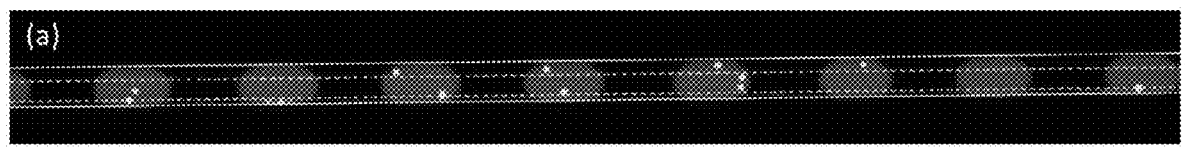
FIG. 30A shows stationary droplets comprising Texas Red fluorescent dye and human breast cancer cells stained with green fluorescent dye before cell lysis.
Figure 30B:
FIG. 30B shows stationary droplets comprising Texas Red fluorescent dye and human breast cancer cells stained with green fluorescence dye during cell lysis with 50.0 V applied to the reservoirs of the anodic auxiliary channel.
Figure 30C:
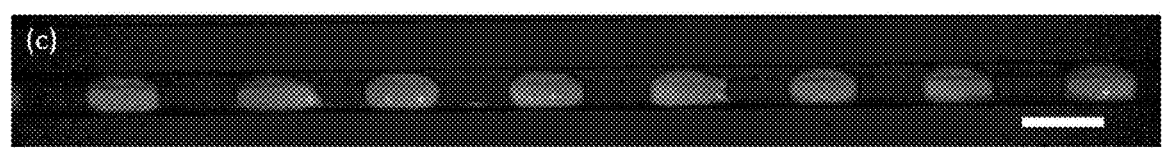
FIG. 30C shows stationary droplets comprising Texas Red fluorescent dye and human breast cancer cells stained with green fluorescent dye after the voltage bias is removed and cell lysis has occurred.

FIGS. 30A, 30B, and 30C show images of the stationary droplets comprising human breast cancer cells before, during, and after cell lysis, respectively. Texas Red fluorescent dye enables tracking of the droplet morphology and anion concentration in the droplet. The cancer cell was stained with Calcein AM green fluorescence dye. In FIG. 30A, before applying the current, the clear images of the droplets with the cells within are shown. In FIG. 30B, the current is applied to the droplet and the Texas Red intensity shows the local fluctuations of concentrations due to the high electric field. The cells started moving by electrophoresis and the induced fluid flow. After the voltage bias is removed, the concentration of the electrolyte is evenly distributed again as it was before applying the current as shown in FIG. 30C. Also evident in FIG. 30C is the absence of a strong peak of the green intensity indicating cell lysis in the droplets.

Without being limited to a particular theory or method, there are three different mechanisms which may explain cell lysis in the droplet. The first is due to the high electric field. The electric current applied to the droplet increases electric field, which is then enhanced further from redistributed electrolyte concentration having highest electric field near the cathodic membrane at the bottom. The high local electric field lyses the cells by breaking the cell membrane. A second mechanism is mechanical cell lysis by fluid shear stress. Inside the depletion zone charge neutrality breaks down resulting in non-zero charge density. The fluid flow is driven by the electric field at this non-zero charge density area and the strong fluid flow mechanically lyses the cells by shear stress. The third mechanism may be osmotic cell lysis. When the electrolyte concentration around the cell is low, the cell uptakes water from the surrounding resulting in swelling over time and eventually cell rupture to the high pressure inside the cell. These mechanisms may also work synergistically to lyse the cells.

Figure 31A:
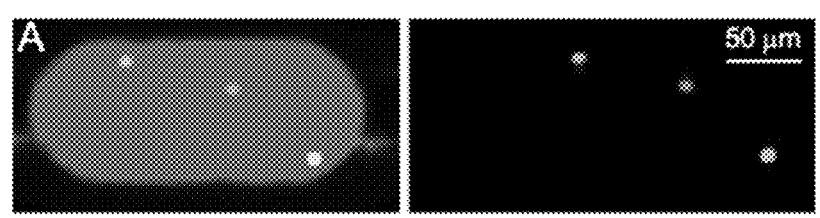
FIG. 31A shows a profile of a droplet comprising Texas Red fluorescent dye and breast cancer cells stained with green fluorescent dye before cell lysis for a droplet containing three breast cancer cells. On the left is a composite micrograph of green and red, and on the right is the corresponding green-only micrograph.
Figure 31B:
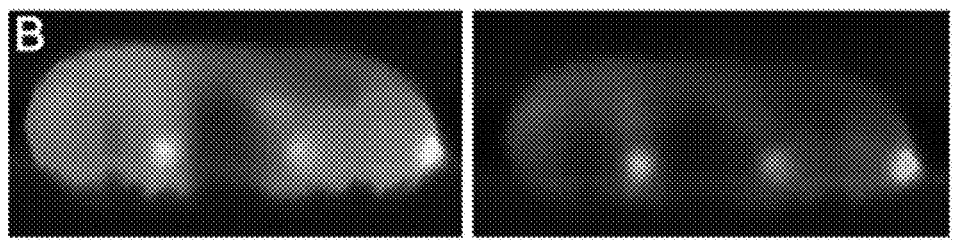
FIG. 31B shows a profile of a droplet comprising Texas Red fluorescent dye and human breast cancer cells stained with green fluorescent dye during cell lysis for a droplet containing three breast cancer cells. On the left is a composite micrograph of green and red, and on the right is the corresponding green-only micrograph.
Figure 31C:
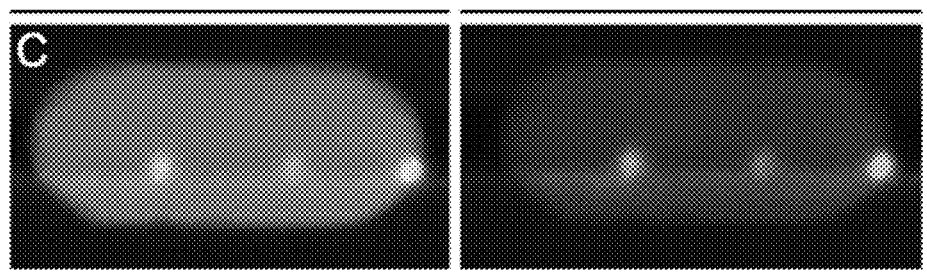
FIG. 31C shows a profile of a droplet comprising Texas Red fluorescent dye and human breast cancer cells stained with green fluorescent dye after cell lysis for a droplet containing three breast cancer cells. On the left is a composite micrograph of green and red, and on the right is the corresponding green-only micrograph.
Figure 31D:
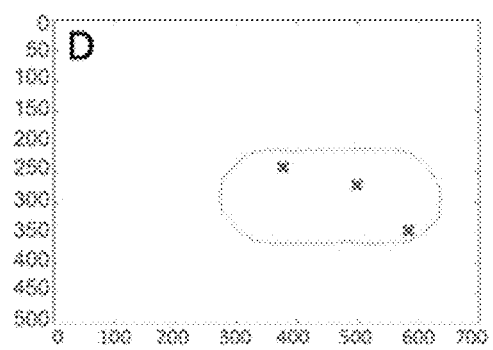
FIG. 31D is a graph of the location of breast cancer cells within a droplet before lysis.
Figure 31E:
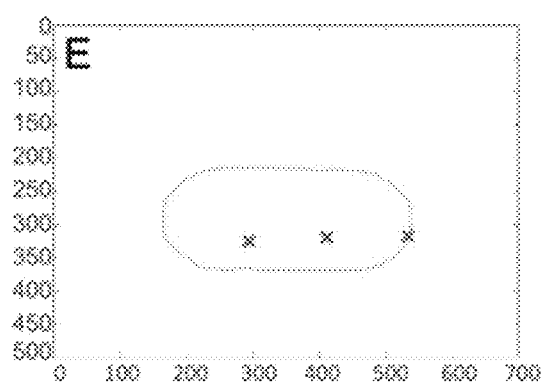
FIG. 31E is a graph of the location of breast cancer cell debris within a droplet during lysis.

FIGS. 31A-31C show a 20× magnified image dataset for electromechanical cell lysis carried out at a voltage of 30 V in droplet containing cells in DEP buffer. FIG. 31B shows the development of IDZs with voltage application. The dispersion of the cell dye due to cell lysis in evident in FIG. 31C, wherein the cell debris are visible as blurred spots. FIGS. 31D and E indicate the location of the cells within the droplet before and during lysis. The cells lyse at the cathodic end of the droplet where the IDZs form, as shown in FIG. 31E. Electroconvection in addition to the high electric field strength at the IDZ boundary likely drive cell lysis at the cathodic end.

Figure 32:
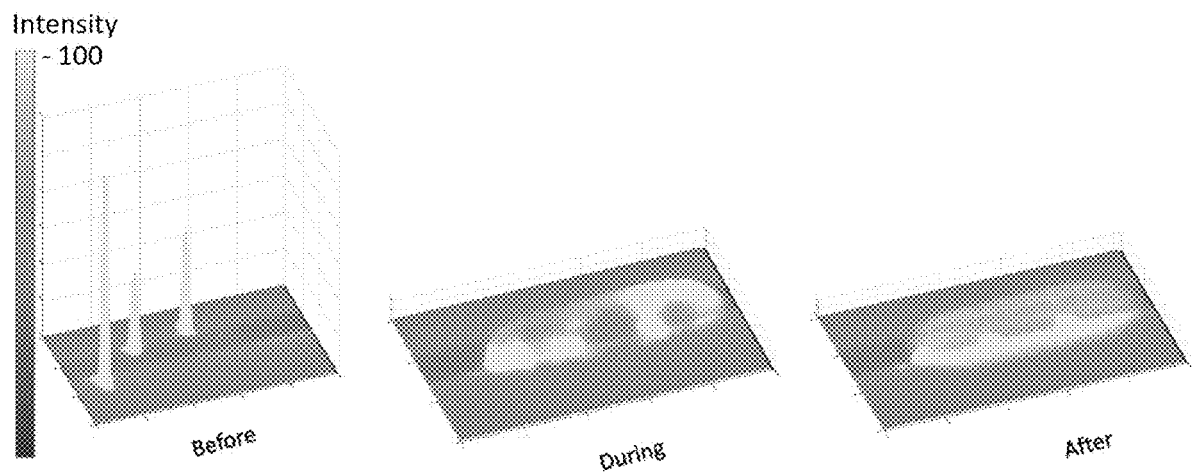
FIG. 32 shows 3D contour plots of green fluorescence intensities before, during, and after cell lysis.

The in-droplet green fluorescence intensities before, during, and after voltage application are plotted in FIG. 32. From these figures, it is demonstrated that cell lysis leads to a significant reduction in green fluorescence intensities with the development of an intensity gradient along the cell boundaries, indicating dye dispersion. These intensity plots are exaggerated to visualize the images having reduced intensities during and after lysis.

ICP-driven in-droplet cell lysis provides several advantages over current in-droplet lysing methods. First, ICP-derived in-droplet lysis is achieved on-demand, which offers the unique advantage of recovering and "locking" the lysed intracellular content within the droplets for analysis. This allows for access to intracellular biomaterials only when triggered to do so. Second, inevitable dilution of droplet contents when using chemical additives is circumvented. Third, ICP-driven lysis is rapid, for example within 10 seconds or less.

Example 9

ICP-Driven Electrokinetic Response in a 1 nL Droplet

In this Example, the characteristic ICP-driven electrokinetic response of a 1 nL droplet was investigated.

The device used in this Example, and in Example 10, is as described above, except that the central main microchannel was 100.0 µm wide, the auxiliary channels were 250.0 µm wide, and the Nafion membrane height was about 10 µm. The spatiotemporal concentration distribution of ionic contents within the droplets was monitored using Texas Red dye-linked BSA as the anionic tracer. The average droplet volume was 1 nL, and the droplets contained 17% v/v OptiPrep, 10 µM Texas Red dye-inked BSA solution, and DEP buffer (pH 7.06, conductivity 1210 mS/cm) containing 10 mM phosphate buffer, 8% sucrose, 0.1% BSA, and 0.3% dextrose.

Voltage was ramped at the rate of 1 V/s across the device and the resulting ionic current was recorded using a picoammeter. In-droplet current response to applied voltage was evaluated by taking current-voltage measurements.

Figure 33:
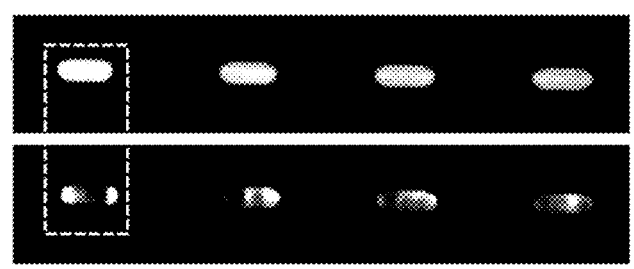
FIG. 33 shows fluorescence micrographs of droplets containing Texas Red dye-linked BSA solution in the absence (top) and presence (bottom) of electric field.
Figure 34:
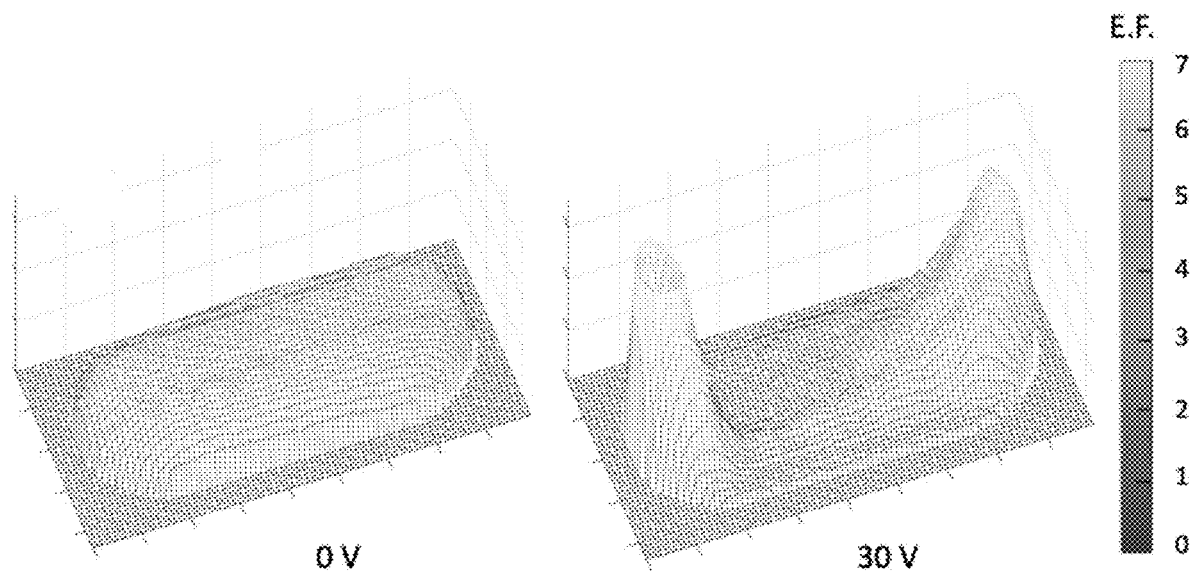
FIG. 34 shows 3D plots showing concentration distribution in a droplet before (left) and during (right) an application of 30 V.

Before the application of a voltage bias, the ionic concentration in the droplet was evenly distributed, as shown in the top row of FIG. 33 and the left plot in FIG. 34. Upon the application of a voltage bias, disruptions in the uniform concentration distribution were immediately observed. This is shown in the bottom row of FIG. 33 and the right plot in FIG. 34. As highlighted in FIGS. 33 and 34, two or more IEZs can be formed simultaneously within a droplet. In the larger 4-10 nL droplets, well-defined IDZ and IEZ zones were observed at the bottom and top halves of the droplets, respectively. In contrast, the formed IEZ in 1 nL droplets tend to confine over the droplet width, and in general occupy the lateral ends of a droplet, when viewed from the top. Without being limited to a particular theory, the indeterminable nature of IEZ and IDZ location is attributed to several factors including comparative dimensions of droplets and IDZ, accelerated IDZ formation and propagation, containment of high electric field within smaller droplet volumes, and differences in droplet composition.

Figure 35:
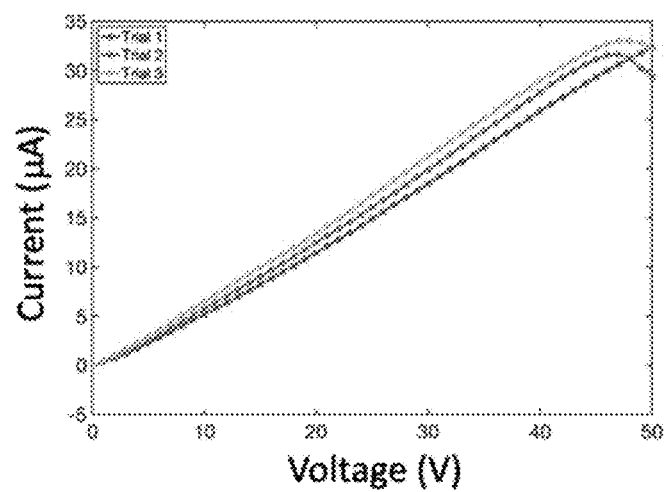
FIG. 35 is a plot of the linear increase in current with voltage for a system with six droplets and a voltage step of 1 V/s.

The current-voltage plot in FIG. 35 shows a linear relationship between the applied volate and the measured current. The gradual tapering of current at higher voltages occurs due to the disruption of electrical contact owing to bubble formation and electrolytic reactions at the leads, such as water oxidation and reduction. The decrease in current at higher voltages is overcome by adding more buffer solution to the auxiliary reservoirs, ensuring ionic contact despite bubble formation. The linear increase in current over the entire voltage range contrasts the typical trend observed for ICP-based enrichment. A typical ICP-based enrichment system operates in three distinct regimes: ohmic, limiting and overlimiting. The local decrease in ionic conductivity due to the formation of the highly resistive IDZ results in the transition from ohmic to limiting regime where the current is limited by mass transport, and therefore plateaus. Although IDZ formation occurs, the limiting regime is not observable here. Without being limited to a particular theory, the hypothesis is that the longitudinal accomplishment of IEZ ensures continued ionic contact, and establishes a closed electrical circuit at all times. The limiting regime is thus bypassed resulting in a linear current-voltage trend.

Figure 36:
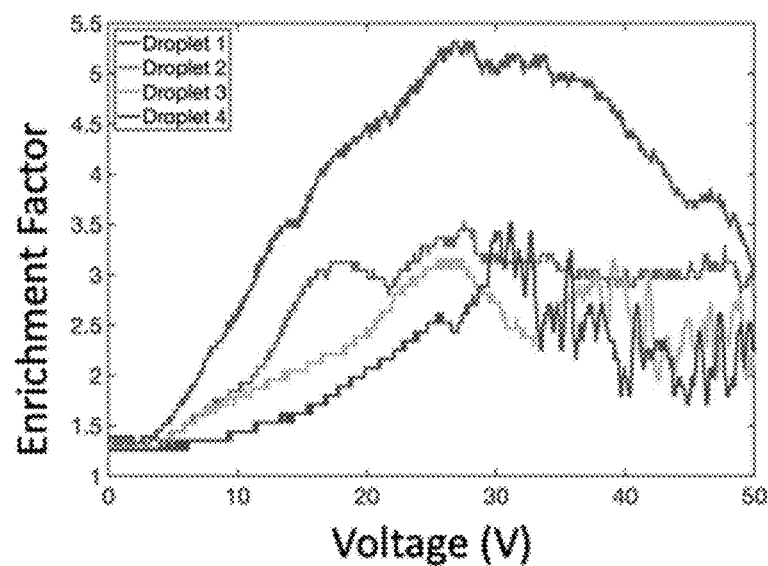
FIG. 36 is a plot showing the variation in enrichment factors with increasing voltage for four droplets.

The local enrichment factors in the droplets were calculated from the image intensities using MATLAB and plotted in FIG. 36. Initially, the local maximum EF increases linearly with voltage reaching a maximum EF in the range of 3 to 5. After reaching a maximum, the EF decreases with increasing voltage. This decrease in EF at very high voltages (>35 V) is due to fluidic instabilities that peak, disintegrating the local enrichment. The variation in points of maxima for individual droplets was expected because of the varying locations of IEZ and IDZ arising from instabilities. It can be noted from FIG. 33 and FIG. 36 that the first droplet from the left exhibits the highest enrichment (>5-fold) while the values range between 3- to 3.5-fold for the other three droplets. The enrichment profile for the leftmost droplet is relatively well-defined with the IEZs located at lateral ends and the IDZ occupying the central domain of the droplet. The noise in the curve for EF is attributed to the electrokinetic instabilities and the blackout between the voltage steps.

The achievement of high local EFs (3- to 5-fold) within nanoliter-scale droplets is a valuable advancement in concentration enrichment in confined volumes. The ability to achieve on-demand concentration enrichment as well as the enriching moving droplets provides for real-time analysis.

Example 10

Enhanced Beta-Galactosidase Assay Sensitivity

In this Example, the applicability of the method to enhance the detection sensitivity of in-droplet beta-galactosidase is demonstrated.

The device utilized for this Example is the same as in Example 9. Beta-galactosidase enzyme is an intracellular enzyme commonly found within the lysosomal lumen and perinuclear region in mammalian cells and is a widely used biomarker for cell senescence. In this Example, ICP-driven cell lysis is applied to recover intracellular beta-galactosidase enzyme for analysis. 1 nL droplets containing breast cancer cells and assay mixture containing fluorogenic fluorescein di-β-D-galactopyranoside (FDG) substrate, Mg++ co-factor, DEP buffer, and Texas Red dye-linked BSA were generated. Texas Red dye-linked BSA was used as an anionic tracer in the background electrolyte to map the concentration distribution in the presence or absence of ICP. A DC voltage of 30 V was applied for 30 seconds to facilitate electromechanical lysis of the encapsulated breast cancer cells. Even though cell lysis can be achieved by applying the voltage for a shorter time, for example 10 seconds, the extended voltage application was performed to ensure complete lysis while providing time for image collection. With cell lysis, the intracellular beta-galactosidase enzyme is released into the encompassing droplet domain triggering the hydrolysis of the FDG substrate by the enzyme to yield fluorescein as the reaction product. Then, a voltage of 30 V is applied a second time after about 25 minutes of incubation at 37° C. The second voltage application step enriches the droplet contents via ICP providing the readout for sensitive detection of the fluorescent assay product. The droplets are imaged at 5-minute intervals, and then 2-minute intervals after readout.

Figure 37A:
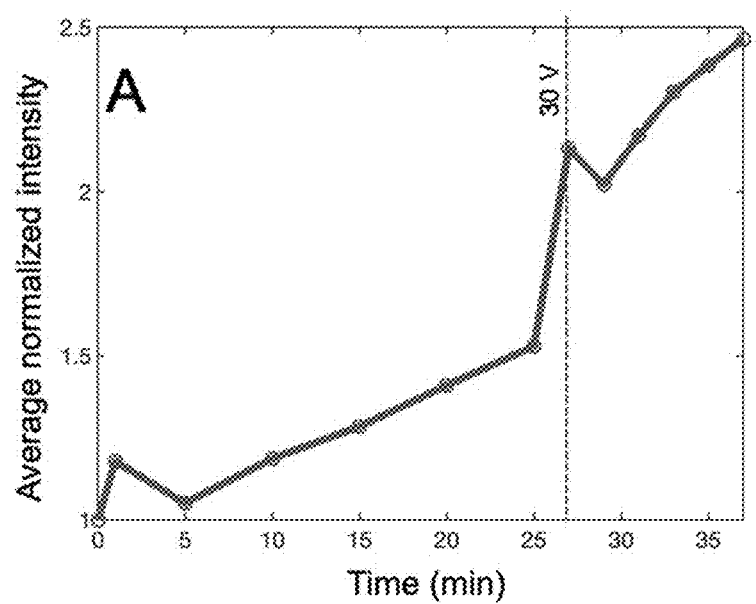
FIG. 37A is a graph of average normalized intensities over time within a droplet that initially contained four cells. Voltage was applied to lyse the cells initially, and then applied again for the readout at 27 minutes.
Figure 37B:
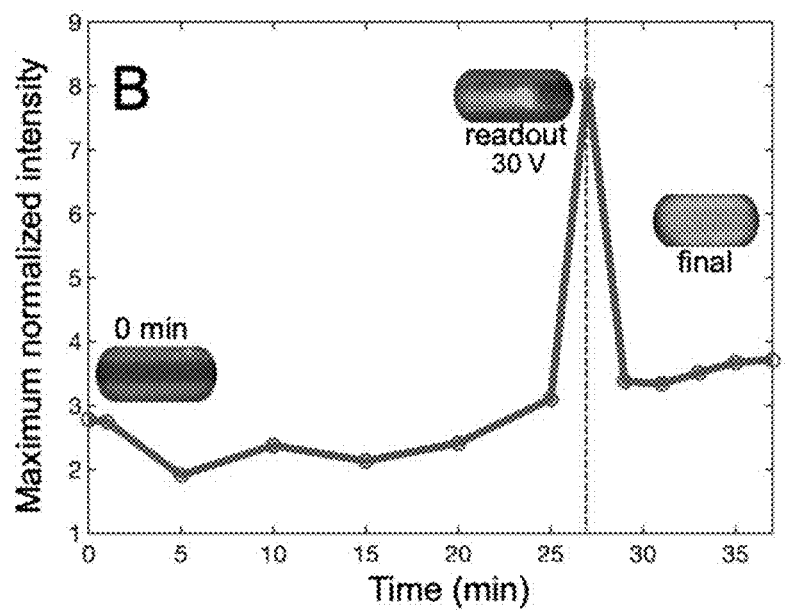
FIG. 37B is a graph of maximum normalized intensities over time within a droplet showing that about 8-fold enrichment is attained at the readout.

FIG. 37A shows the ICP-driven increase in average normalized intensities over time, for a droplet initially containing four cells. The average droplet intensities at each datapoint are normalized with the initial average intensity of the droplet. The calculated intensities are therefore termed "average normalized intensities" except at the voltage application step, wherein the normalized intensity is termed as EF. ICP is first used to lyse the cells 30 seconds after application of the voltage. A spike in normalized intensity at 1 minute denotes local enrichment of lysate and possible formation of assay products and their enrichment with ICP. In the period ranging from 5-25 minutes, the device and droplet is incubated in the absence of electric field. The increase in the average normalized intensities over this period follow a gradual linear trend. With the application of a voltage of 30 V at 27 minutes, a high average enrichment factor is achieved. This provides the readout for the sensitive detection of enzyme activity. The curve for normalized intensities following the readout exhibit a much steeper increase compared to that in the 5-25 minute range, indicating the possibility in the enhancement of reaction rate with ICP. The maximum normalized intensities for the droplet over the assay time are shown in FIG. 37B, with the composite images of the droplet at the start of the experiment, at readout (30 V, 27 minutes) and at the end (37 minutes) shown as insets. The enrichment of product at readout are indicated by the bright spots and an increase in the in-droplet green fluorescence intensity is evident from these insets.

Figure 37C:
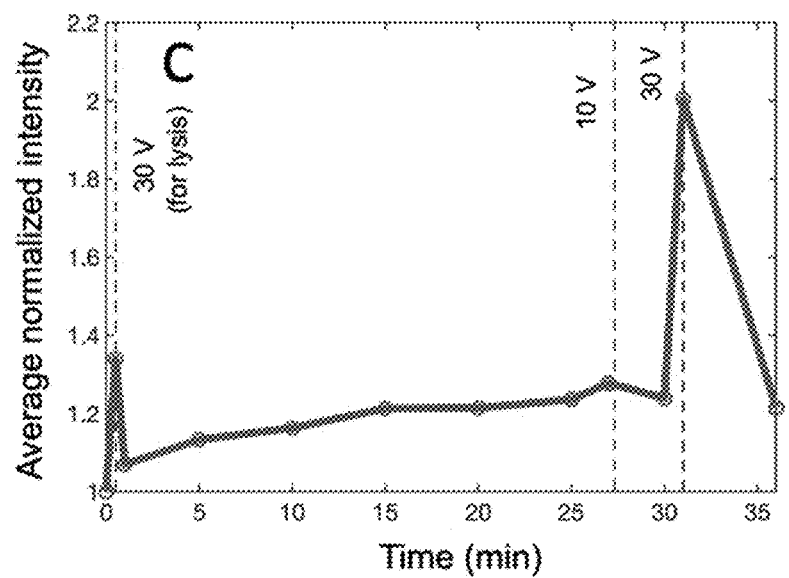
FIG. 37C is a plot of average normalized intensity over time showing the variation in in-droplet intensity with a magnitude of applied voltage at the readout. A voltage of 10 V facilitates a lower enrichment of 1.3-fold compared to 2-fold at 30 V.
Figure 37D:
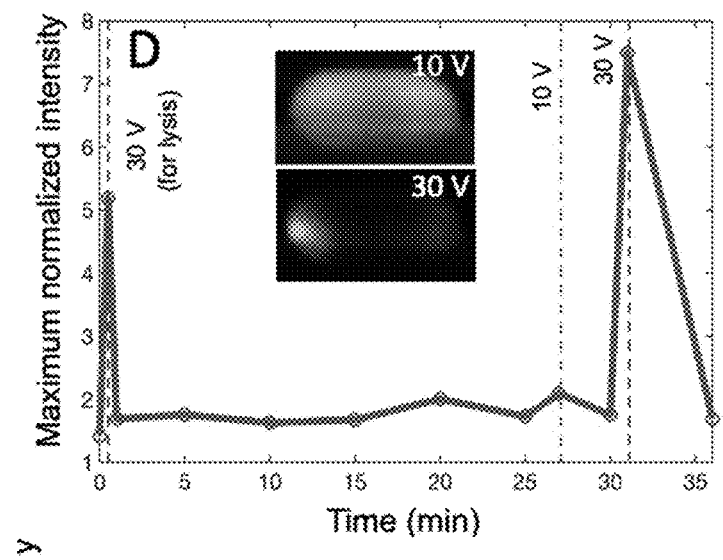
FIG. 37D is a plot of maximum normalized intensity over time displaying the variation in maximum enrichment factors with applied voltage at readout. A voltage of 10 V renders about 2-fold enrichment while 30 V facilitates about 7.6-fold enrichment.

Two voltage conditions of 10 V and 30 V were tested at 27 minutes and 30 minutes of assay time, respectively. FIGS. 37C and 37D show the average and maximum normalized intensities for a droplet containing four cells, with composite images shown as insets. At the start a voltage bias of 30 V was applied for 30 seconds to lyse the cells. Thereafter, the device was incubated at 37° C. before applying a voltage of 10 V at 27 minutes. The voltage application was then stopped and the droplet images 3 minutes later, at 30 minutes with no applied voltage. Then 30 V was applied for a second readout. It was found that the signal intensity and therefore the EF are higher at the voltage bias of 30 V as compared to that at 10V. This result is in consonance with the claim that concentration enrichment correlates with the magnitude of applied voltage.

Figure 37E:
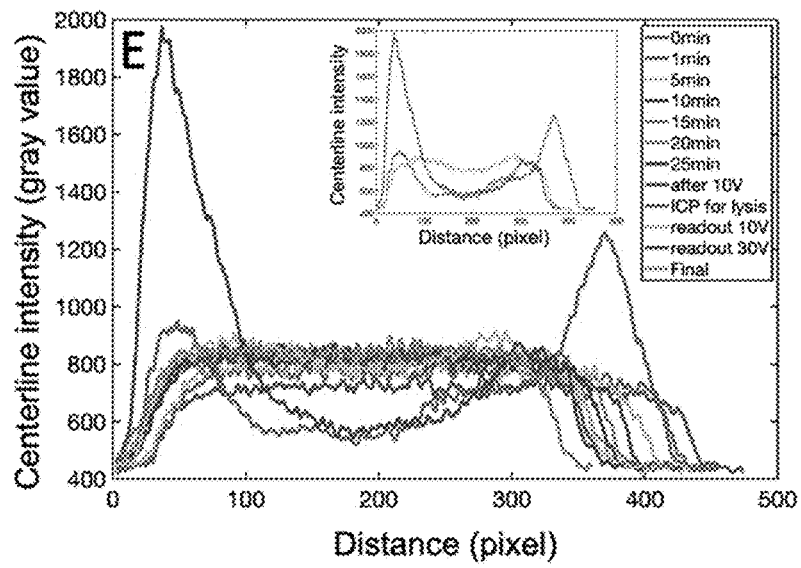
FIG. 37E shows the centerline intensities across the longitudinal midline of a droplet over various time intervals. The centerline intensities consistently increase with time. The inset shows the intensity profile during voltage application.
Figure 37F:
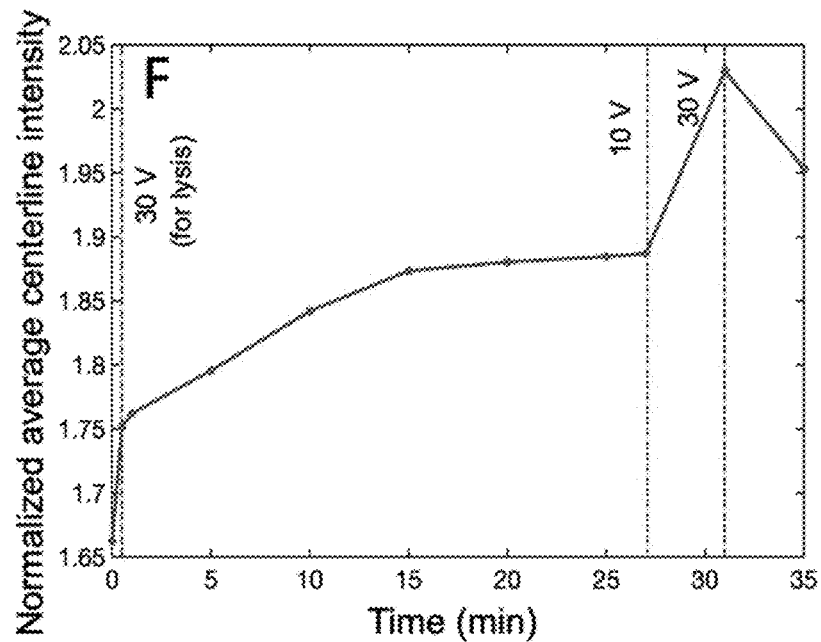
FIG. 37F shows the normalized average centerline intensity over time wherein the intensities increase gradually and plateau before peaking at the readout at 30 V.

Additionally, the intensity profiles across the centerline of the droplets were evaluated. Such calculations exclude any superfluous intensities due to the overlap of a droplet with the Nafion membranes that exhibit intrinsic fluorescent intensity. ImageJ software was used to map the intensity profile measured along a line that was drawn horizontally through the center of a droplet's projected area. The intensity profiles for a given droplet were evaluated at periodic data points during the assay time and are shown in FIG. 37E. The centerline intensities were found to steadily increase with time. The centerline intensity exhibited peaks with voltage application, indicating concentration enrichment. The average centerline intensities were calculated by taking the average of the intensities along the centerline and dividing it by the baseline intensity of 400, as shown in FIG. 37F. A steep gradient in slop was observed with application of voltage bias initially for lysis and a much steeper slope was observed at readout.

Figure 38A:
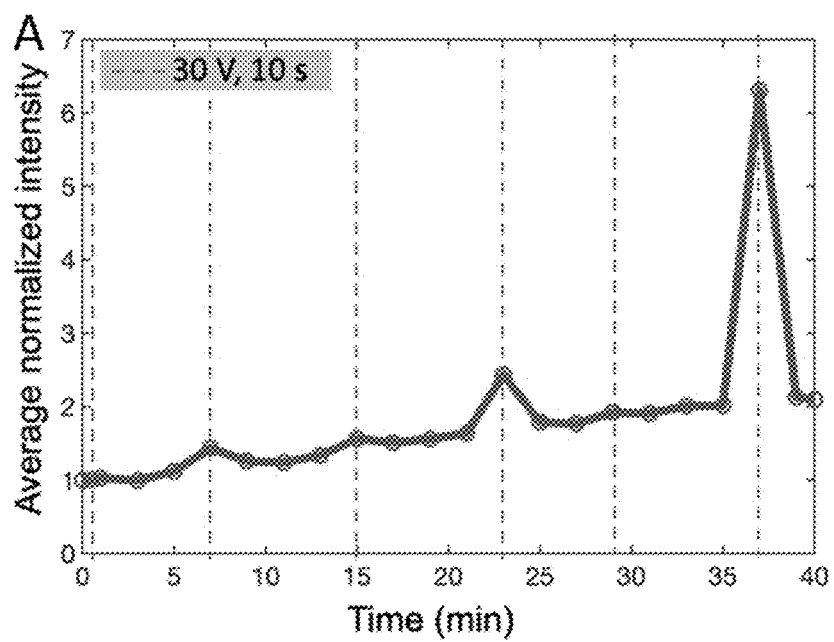
FIG. 38A is a plot of average normalized intensity over time and with intermittent application of a voltage of 30 V for 10 seconds.
Figure 38B:
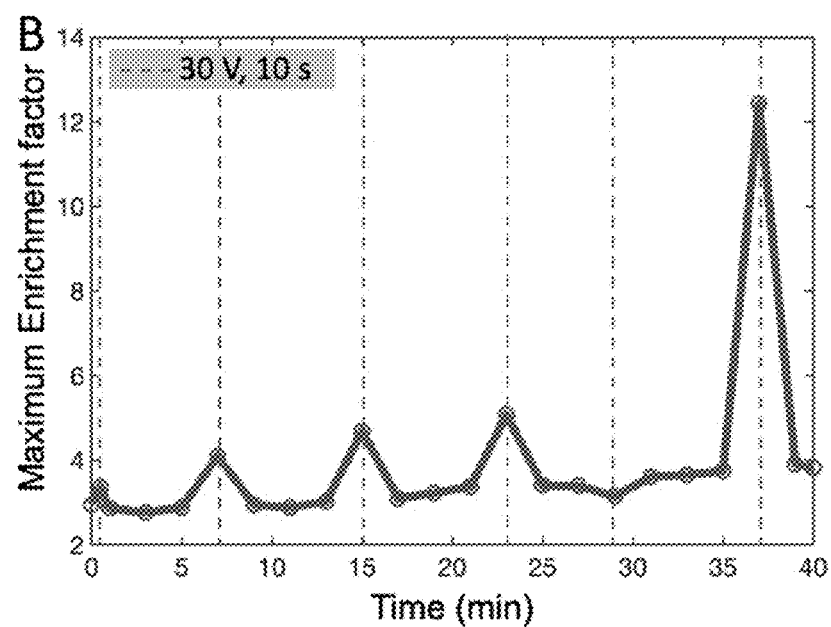
FIG. 38B is a plot of maximum enrichment factor over time and with intermittent application of a voltage of 30 V for 10 seconds.
Figure 39:
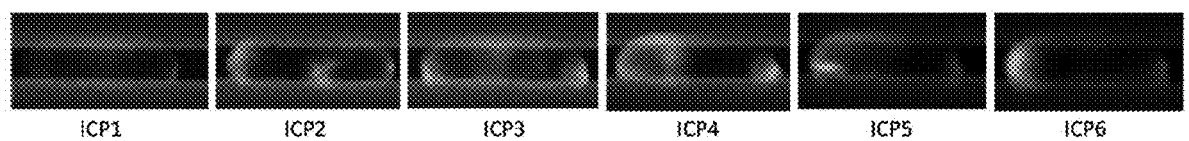
FIG. 39 shows the distribution of green fluorescent intensities for progressive voltage application steps.

The influence of ICP in enhancing the enzymatic reaction involving the intermittent application of voltage was investigated. At each ICP step, a voltage of 30 V was applied for 10 seconds. To assess the progression of the enzymatic reaction, maximum and average enrichment factors for the whole droplets were calculated. The maximum enrichment factor was calculated by dividing the maximum intensity value in a droplet domain by the average initial intensity over the projected droplet area. The average EF is calculated by dividing the average intensity by the average initial intensity in the droplet area. FIG. 38 shows a plot of average normalized intensity over time. The blue dotted lines represent the voltage application at the given time point. FIG. 38B is a plot of maximum EF over time, with the same blue dotted lines representing the voltage application. Over 12-fold enrichment is achieved at the final readout at 37 minutes. FIG. 39 show the in-droplet distribution of green fluorescent intensities at each ICP point, represented by the blue dotted lines in FIGS. 38A and 38B.

Without being limited to a particular theory, intermittent voltage application results in the linear enhancement in enzymatic reaction rate. This decreases the required amount of time for detection of assay activity by increasing assay sensitivity which provides for in-droplet on-demand cell lysis and cell-specific lysate recovery and analysis.

While this invention may be embodied in many different forms, the described scientific papers and other referenced materials mentioned herein are incorporated by reference in their entirety. Furthermore, the invention encompasses any possible combination of some or all of the various embodiments mentioned herein, described herein and/or incorporated herein. In addition, the invention encompasses any possible combination that also specifically excludes any one or some of the various embodiments mentioned herein, described herein and/or incorporated herein.

The present disclosure is further defined by the following numbered paragraphs:

1. A microfluidic device comprising:
    at least one fluidic main microchannel, wherein the one or more fluidic main microchannel is connected to at least one inlet and at least one outlet, wherein water-in-oil droplets are infused through the at least one of the inlet(s), flow through the at least one main microchannel, and are withdrawn from at least one of the outlet (s); and at least two permselective membranes, wherein a portion of each membrane extends into the main microchannel along a portion of the length of the main microchannel and a portion of each membrane extends outside of the main microchannel for electrical connection, wherein the droplets are in simultaneous contact with a portion of the permselective membranes as the droplets flow through the main microchannel, and wherein a voltage bias is applied across the permselective membranes for in-droplet enrichment and separation of charged species within the droplet.

2. The device according to paragraph 1, wherein the at least one main microchannel comprises two permselective membranes.

3. The device according to paragraph 2, wherein the permselective membranes extend into the main microchannel on opposite sides of the main microchannel.

4. The device of any one of paragraphs 1 to 3, wherein the permselective membranes extend into the main microchannel for about the entire length of the main microchannel.

5. The device of any one of paragraphs 1 to 3, wherein the permselective membranes extend into the main microchannel for at least about half the length of the main microchannel.

6. The device of any one of paragraphs 1 to 3, wherein the permselective membranes extend into the main microchannel for at least about three-quarters the length of the main microchannel.

7. The device of any one of paragraphs 1 to 6, further comprising at least two auxiliary channels wherein the portion of the permselective membrane that extends outside of the main microchannel extends into a portion of an auxiliary channel wherein the auxiliary channel comprises an electrolyte solution, and wherein the permselective membranes do not extend into the same auxiliary channel.

8. The device of paragraph 7, wherein the auxiliary channel further comprises driving electrodes to apply the voltage bias across the permselective membranes.

9. The device of any one of paragraphs 1 to 8, wherein the permselective membranes are cation-selective.

10. The device of any one of paragraphs 1 to 8, wherein the permselective membranes are anion-selective.

11. The device of any one of paragraphs 1 to 10, wherein the device comprises more than one main microchannel in fluid connection with a singular inlet.

12. The device of any one of paragraphs 1 to 10, wherein the device comprises more than one main microchannel in fluid connection with more than one inlets.

13. the device of any one of paragraphs 1 to 12, wherein the device comprises more than one main microchannel in fluid connection with a singular outlet.

14. The device of any one of paragraphs 1 to 12, wherein the device comprises more than one main microchannel in fluid connection with more than one outlet.

15. The device of any one of paragraphs 1 to 14, wherein the device comprises more than one main microchannel, and wherein any two permselective membranes extends into only one main microchannel.

16. The device of any one of paragraphs 1 to 14, wherein the device comprises more than one main microchannel, and wherein at least one permselective membrane extends into a portion of more than one main microchannel.

17. The device of any one of paragraphs 7 to 16, wherein the device comprises more than one main microchannel, and wherein the permselective membranes each extend into a unique auxiliary channel.

18. The device of any one of paragraphs 7 to 16, wherein the device comprises more than one main microchannel, and wherein at least two permselective membranes extend into the same auxiliary channel.

19. The device of any one of paragraphs 1 to 18, wherein the permselective membranes have a size and dimension such that the membranes run parallel on either side of the at least one main microchannel and extend into the main microchannel along the length of the main microchannel for a length necessary for ion concentration polarization to occur across the entire droplet volume as the droplet flows through the main microchannel.

20. The device of any one of paragraphs 1 to 19, wherein ion concentration polarization occurs over the entire droplet volume.

21. The device of any one of paragraphs 1 to 20, further comprising uniform flow of the droplets from the at least one inlet to the at least one outlet.

22. The device of paragraph 21, wherein uniform flow is ensured by a pump at an inlet to infuse the droplets into the device.

23. The device of paragraph 19, wherein uniform flow is ensured by a pump at an outlet to withdraw the droplets from the device.

24. The device of paragraph 19, wherein uniform flow is ensured by a syringe at an inlet to infuse the droplets into the device.

25. The device of paragraph 19, wherein uniform flow is ensured by a syringe at an outlet to withdraw the droplets from the device.

26. The device of any one of paragraphs 1 to 25, wherein the droplet flow rate is from about 0.0 µm/s to about 5000 µm/s.

27. The device of any one of paragraphs 1 to 26, wherein droplets flow from inlet to outlet in at least about 20 seconds.

28. The device of any one of paragraphs 1 to 26, wherein droplets flow from inlet to outlet in at least about 15 seconds.

29. The device of any one of paragraphs 1 to 26, wherein droplets flow from inlet to outlet in at least about 10 seconds.

30. The device of any one of paragraphs 1 to 26, wherein droplets flow from inlet to outlet in at least about 5 seconds.

31. The device of any one of paragraphs 1 to 26, wherein droplets flow from inlet to outlet in at least about 1 second.

32. The device of any one of paragraphs 1 to 31, wherein the at least one main microchannel has a length of about 5.0 mm to about 100 mm.

33. The device of any one of paragraphs 1 to 32, wherein the at least one main microchannel has a width of about 10 µm to about 1000

34. The device of any one of paragraphs 1 to 33, wherein the main microchannel has a height of about 10 µm to about 1000

35. The device of any one of paragraphs 1 to 33, wherein the walls, ceiling, and/or floor of the main microchannel comprise polydimethylsiloxane ("PDMS"), polymethylmethacrylate ("PMMA"), polystyrene, polycarbonate, cyclic olefin polymer, cyclic olefin copolymer, pressure sensitive adhesive tape, silicon, glass, resin of a 3D printer, polyethylene glycol, crosslinked polyethylene glycol diacrylate ("PEGDA") resin, or combinations thereof.

36. The device of any one of paragraphs 1 to 35, wherein the volume of the droplets is from about 10 pL to about 50.0 nL.

37. The device of any one of paragraphs 1 to 36, wherein the droplets comprise proteins, antigens, bioparticles, bacteria, virus, nucleic acids, enzymes, biological cells, DNA, RNA, aptamers, antibodies, peptides, peptide nucleic acids, morpholino oligonucleotides, receptors, other bioparticles, other nano particles, or a combination thereof.

38. The device of any one of paragraphs 1 to 37, wherein the droplets comprise blood, blood plasma, saliva, urine, sweat, tears, or any other such biofluid or any combination thereof 39. The device of any one of paragraphs 1 to 38, wherein the droplets comprise an electrolyte solution.

40. The device of paragraph 39, wherein the droplets comprise phosphate buffer, Tris buffer, and/or combinations thereof.

41. The device of any one of paragraphs 1 to 40, wherein the length of the permselective membranes is from about 1.0 mm to about 100 mm.

42. The device of any one of paragraphs 1 to 41, wherein the width of the permselective membranes is from about 50 μm to about 1000 μm.

43. The device of any one of paragraphs 1 to 42, wherein the thickness of the permselective membranes is from about 1.0 μm to about 50 μm.

44. The device of any one of paragraphs 7 to 43, wherein the auxiliary microchannels have a length of about 2.0 mm to about 100 mm.

45. The device of any one of paragraphs 7 to 44, wherein the auxiliary microchannels have a width of about 10 μm to about 1000 μm.

46. The device of any one of paragraphs 7 to 45, wherein the auxiliary microchannels have a height of about 10 μm to about 1000 μm.

47. The device of any one of paragraphs 7 to 44, wherein the walls, ceiling, and/or floor of the main microchannel comprise polydimethylsiloxane ("PDMS"), polymethylmethacrylate ("PMMA"), polystyrene, polycarbonate, cyclic olefin polymer, cyclic olefin copolymer, pressure sensitive adhesive tape, silicon, glass, resin of a 3D printer, polyethylene glycol, crosslinked polyethylene glycol diacrylate ("PEGDA") resin, or combinations thereof.

48. The device of any one of paragraphs 7 to 47, wherein the electrolyte solution within the auxiliary channels comprises NaCl, KCl, $Na_2SO_4$, HCl, $H_2SO_4$, NaOH, KOH, $NaNO_3$, $KNO_3$, phosphate buffer, carbonate buffer, acetate buffer, borate buffer, Tris buffer, HEPES (4-(2-hydroxyethyl)-1-piperazineethanesulfonic acid), MOPS (3-(N-morpholino) propanesulfonic acid), TAE (Tris-acetate-EDTA), PIPES (piperazine-N,N'-bis(2-ethanesulfonic acid), tricine buffer, PBS (phosphate buffered saline) and/or combinations thereof.

49. The device of any one of paragraphs 1 to 48, wherein the outlet is connected to a droplet splitting device.

50. The device of any one of paragraphs 1 to 48, wherein the outlet collects the droplets for further analytics and/or for further processing.

51. The device of any one of paragraphs 1 to 50, wherein the voltage applied to the permselective membranes is between about 0 and about 500 V.

52. The device of any one of paragraphs 7 to 50, wherein the voltage applied to the electrolyte solution in the auxiliary channel is between about 0 V and about 500 V.

53. A method for concentration enrichment of charged species within a droplet comprising: flowing water-in-oil droplets through at least one main microchannel of the microfluidic device of any one of paragraphs 1-52; and applying a voltage bias across the permselective membranes for a period of time so that ion concentration polarization occurs and therefore enrichment of charged species within a portion of the droplet.

54. The method of paragraph 53, wherein charged species are enriched 2- to 20-fold.

55. The method of paragraph 53, wherein the permselective membranes are cation-selective leading to concentration enrichment of anions in the droplet.

56. The method of paragraph 53, wherein the permselective membranes are anion-selective leading to a concentration enrichment of cations in the droplet.

57. The method of any one of paragraphs 53 to 56, wherein separation of charged species of varying and/or distinct electrophoretic mobilities occurs within a single droplet.

58. A method for ion exchange between the droplet and the electrolyte solution in an auxiliary channel comprising:
flowing water-in-oil droplets through at least one main microchannel of the microfluidic device of any one of paragraphs 7 to 52; and
applying a voltage bias across the permselective membranes for a period of time so that ions are injected into the droplet from an auxiliary channel at the enriched portion of the droplet and ions are simultaneously ejected from the microdroplet into another auxiliary channel at the ion depleted portion of the droplet.

59. The method of paragraph 58, wherein the permselective membranes are cation-selective and cation exchange occurs between the droplet and the electrolyte solution in an auxiliary microchannel.

60. The method of paragraph 58, wherein the permselective membranes are anion-selective and anion exchange occurs between the droplet and the electrolyte solution in an auxiliary microchannel.

61. The method of any one of paragraphs 58 to 60, wherein the electrolyte within the electrolyte solution is selected for specific ion exchange.

62. A method for cell lysis within a droplet comprising:
flowing water-in-oil droplets comprising at least one cell through at least one main microchannel of the microfluidic device of any one of paragraphs 1 to 52; and
applying a voltage bias across the permselective membranes for a period of time so that cell lysis occurs within the droplet and the lysate is enriched and/or separated within the droplet.

The above disclosure is intended to be illustrative and not exhaustive. This description will suggest many variations and alternatives to one of ordinary skill in this art. All these alternatives and variations are intended to be included within the scope of the following claims where the term "comprising" means "including, but not limited to". Those familiar with the art may recognize other equivalents to the specific embodiments described herein which equivalents are also intended to be encompassed by the following claims.

What is claimed is:

1. A microfluidic device comprising: at least one main microchannel, wherein the one or more main microchannel is connected to at least one inlet and at least one outlet, wherein water-in-oil droplets are infused through the at least one of the inlet(s), flow through the at least one main microchannel, and are withdrawn from at least one of the outlet(s);

at least two permselective membranes, wherein a portion of each permselective membrane extends into the main microchannel along a portion of the length of the main microchannel and a portion of each permselective membrane extends outside of the main microchannel for electrical connection; and at least two auxiliary channels wherein the portion of the permselective membrane that extends outside of the main microchannel extends into a portion of an auxiliary channel wherein the auxiliary channel comprises an electrolyte solution, and wherein the permselective membranes do not extend into the same auxiliary channel, wherein the water-in-oil droplets are in simultaneous contact with a portion of the permselective membranes as the water-in-oil droplets flow through the main microchannel, wherein the permselective membranes is configured to allow ion exchange to occur between the water-in-oil droplet and the electrolyte solution, and wherein a voltage bias is applied across the permselective membranes for in-droplet enrichment and separation of charged species within the water-in-oil droplet.

2. The device of claim 1, wherein the permselective membranes extend into the main microchannel on opposite sides of the main microchannel, and extend into the main microchannel for at least about half the length of the main microchannel.

3. The device of claim 1, wherein the auxiliary channels further comprise driving electrodes to apply the voltage bias across the permselective membranes.

4. The device of claim 1, wherein the permselective membranes are cation-selective.

5. The device of claim 1, wherein the device comprises more than one main microchannel in fluid connection with the singular inlet or more than one inlet, and in fluid connection with the singular outlet or more than one outlet.

6. The device of claim 1, wherein the device comprises more than one main microchannel, and wherein any two permselective membranes extends into only one main microchannel, and wherein the permselective membranes each extend into one of the auxiliary channels.

7. The device of claim 1, wherein the device comprises more than one main microchannel, and wherein at least one permselective membrane extends into a portion of more than one main microchannel, and wherein at least two permselective membranes extend into the same auxiliary channel.

8. The device of claim 1, wherein the permselective membranes have a size and dimension such that the permselective membranes run parallel on either side of the at least one main microchannel and extend into the main microchannel along the length of the main microchannel for a length necessary for ion concentration polarization to occur across the entire droplet volume as the water-in-oil droplet flows through the main microchannel.

9. The device of claim 1, further comprising uniform flow of the water-in-oil droplets from the at least one inlet to the at least one outlet, wherein uniform flow is ensured by a pump at an inlet to infuse the water-in-oil droplets into the device, or a pump at an outlet to withdraw the water-in-oil droplets from the device, or a syringe at an inlet to infuse the water-in-oil droplets into the device, or a syringe at an outlet to withdraw the water-in-oil droplets from the device, wherein the water-in-oil droplet flow rate is from about 0.0 μm/s to about 5000 μm/s.

10. The device of claim 1, wherein the at least one main microchannel has a length of about 5.0 mm to about 100 mm, a width of about 10 μm to about 1000 μm, and a height of about 10 μm to about 1000 μm.

11. The device of claim 1, wherein the walls, ceiling, and/or floor of the main microchannel comprise polydimethylsiloxane ("PDMS"), polymethylmethacrylate ("PMMA"), polystyrene, polycarbonate, cyclic olefin polymer, cyclic olefin copolymer, pressure sensitive adhesive tape, silicon, glass, resin of a 3D printer, polyethylene glycol, crosslinked polyethylene glycol diacrylate ("PEGDA") resin, or combinations thereof.

12. The device of claim 1, wherein the volume of the water-in-oil droplets is from about 10 pL to about 50.0 nL, and wherein the water-in-oil droplets comprise an electrolyte solution and proteins, antigens, bioparticles, bacteria, virus, nucleic acids, enzymes, biological cells, DNA, RNA, aptamers, antibodies, peptides, peptide nucleic acids, morpholino oligonucleotides, receptors, other bioparticles, other nano particles, blood, blood plasma, saliva, urine, sweat, tears, or any other such biofluid, or any combination thereof.

13. The device of claim 1, wherein the length of the permselective membranes is from about 1.0 mm to about 100 mm, width of the permselective membranes is from about 50 μm to about 1000 μm, and the thickness of the permselective membranes is from about 1.0 μm to about 50 μm.

14. The device of claim 1, wherein the auxiliary microchannels have a length of about 2.0 mm to about 100 mm, a width of about 10 μm to about 1000 μm, and a height of about 10 μm to about 1000 μm.

15. The device of claim 1, wherein the walls, ceiling, and/or floor of the main microchannel comprise polydimethylsiloxane ("PDMS"), polymethylmethacrylate ("PMMA"), polystyrene, polycarbonate, cyclic olefin polymer, cyclic olefin copolymer, pressure sensitive adhesive tape, silicon, glass, resin of a 3D printer, polyethylene glycol, crosslinked polyethylene glycol diacrylate ("PEGDA") resin, or combinations thereof, and wherein the electrolyte solution within the auxiliary channels comprises NaCl, KCl, $Na_2SO_4$, HCl, $H_2SO_4$, NaOH, KOH, $NaNO_3$, $KNO_3$, phosphate buffer, carbonate buffer, acetate buffer, borate buffer, Tris buffer, HEPES (4-(2-hydroxyethyl)-1-piperazineethanesulfonic acid), MOPS (3-(N-morpholino) propanesulfonic acid), TAE (Tris-acetate-EDTA), PIPES (piperazine-N,N'-bis(2-ethanesulfonic acid), tricine buffer, PBS (phosphate buffered saline) and/or combinations thereof.

16. The device of claim 1, wherein the voltage applied to the permselective membranes is between about 0 and about 500 V, and the voltage applied to the electrolyte solution in the auxiliary channel is between about 0 V and about 500 V.

17. A method for concentration enrichment of charged species within a droplet comprising:
flowing water-in-oil droplets through at least one main microchannel of the microfluidic device of claim 1; and
applying a voltage bias across the permselective membranes for a period of time so that ion concentration polarization occurs and therefore enrichment of charged species within a portion of the droplet, wherein charged species are enriched 2- to 20-fold.

18. The method of claim 17, wherein separation of charged species of varying and/or distinct electrophoretic mobilities occurs within a single droplet.

19. A method for ion exchange between the droplet and the electrolyte solution in an auxiliary channel comprising:
- flowing water-in-oil droplets through at least one main microchannel of the microfluidic device of claim 1; and
- applying a voltage bias across the permselective membranes for a period of time so that ions are injected into the droplet from an auxiliary channel at the enriched portion of the droplet and ions are simultaneously ejected from the microdroplet into another auxiliary channel at the ion depleted portion of the droplet, wherein the permselective membranes are cation-selective and cation exchange occurs between the droplet and the electrolyte solution in an auxiliary microchannel or the permselective membranes are anion-selective and anion exchange occurs between the droplet and the electrolyte solution in an auxiliary microchannel.

20. A method for cell lysis within a droplet comprising:
- flowing water-in-oil droplets comprising at least one cell through at least one main microchannel of the microfluidic device of claim 1; and
- applying a voltage bias across the permselective membranes for a period of time so that cell lysis occurs within the droplet and the lysate is enriched and/or separated within the droplet.

* * * * *